US008845975B2

(12) United States Patent
Henstock et al.

(10) Patent No.: US 8,845,975 B2
(45) Date of Patent: Sep. 30, 2014

(54) METHOD OF CONTROLLING THE PRODUCTION OF SILVER CHLORIDE ON A SILVER CATALYST IN THE PRODUCTION OF ALKYLENE OXIDES

(75) Inventors: William H. Henstock, Charleston, WV (US); Juliana G. Serafin, Charleston, WV (US); Albert C. Liu, Charleston, WV (US); Hwaili Soo, Charleston, WV (US); Yujun Liu, Pearland, TX (US); Manuk Colakyan, South Charleston, WV (US); Sagar Petkar, Pune (IN)

(73) Assignee: Dow Technology Investments LLC, Midland, MI (US)

( * ) Notice: Subject to any disclaimer, the term of this patent is extended or adjusted under 35 U.S.C. 154(b) by 762 days.

(21) Appl. No.: 12/974,439

(22) Filed: Dec. 21, 2010

(65) Prior Publication Data

US 2011/0160470 A1    Jun. 30, 2011

Related U.S. Application Data

(60) Provisional application No. 61/290,357, filed on Dec. 28, 2009.

(51) Int. Cl.
| | |
|---|---|
| *B01J 8/00* | (2006.01) |
| *C07D 301/03* | (2006.01) |
| *C07D 301/10* | (2006.01) |
| *C07D 301/36* | (2006.01) |
| *C07D 301/32* | (2006.01) |

(52) U.S. Cl.
CPC ............ *C07D 301/10* (2013.01); *C07D 301/36* (2013.01); *C07D 301/32* (2013.01)
USPC ............................ 422/187; 549/536; 549/534

(58) Field of Classification Search
USPC .................................. 549/536, 534; 422/187
See application file for complete search history.

(56) References Cited

U.S. PATENT DOCUMENTS

| 2,895,918 A | 7/1959 | MacCormack |
|---|---|---|
| 3,265,757 A | 8/1966 | Frevel et al. |

(Continued)

FOREIGN PATENT DOCUMENTS

| CA | 1286687 | 7/1991 |
|---|---|---|
| CN | 1035624 A | 9/1989 |

(Continued)

OTHER PUBLICATIONS

Kirk-Othmer, Encyclopedia of Chemical Technology, copyright John-Wiley and Sons, vol. 10, p. 632-673, published online (2004).*

(Continued)

*Primary Examiner* — T. Victor Oh
(74) *Attorney, Agent, or Firm* — Hansen IP Law PLLC

(57) ABSTRACT

A plant and process for producing alkylene oxides to control the production of silver chloride on a high efficiency silver catalyst is disclosed and described. The process involves reacting an alkylene and an organic chloride gas phase promoter with oxygen over the high efficiency silver catalyst. The sulfur concentration in the alkylene oxide reactor feed is controlled to reduce the production of silver chloride which acts as a catalyst poison.

20 Claims, 5 Drawing Sheets

(56) References Cited

U.S. PATENT DOCUMENTS

| | | | |
|---|---|---|---|
| 3,315,003 | A | 4/1967 | Khelghatian |
| 3,844,981 | A | 10/1974 | Cusumano |
| 4,130,570 | A | 12/1978 | Boreskov et al. |
| 4,455,446 | A | 6/1984 | Brownell et al. |
| 4,759,313 | A | 7/1988 | Dye |
| 4,761,394 | A | 8/1988 | Lauritzen |
| 4,766,105 | A * | 8/1988 | Lauritzen ............ 502/216 |
| 4,769,047 | A | 9/1988 | Dye |
| 4,808,738 | A | 2/1989 | Lauritzen |
| 4,820,675 | A | 4/1989 | Lauritzen |
| 4,829,044 | A | 5/1989 | Boxhoorn |
| 4,830,733 | A | 5/1989 | Nagji et al. |
| 4,835,338 | A | 5/1989 | Liu |
| 4,874,739 | A | 10/1989 | Boxhoorn |
| 4,874,879 | A | 10/1989 | Lauritzen |
| 5,114,689 | A | 5/1992 | Nagji et al. |
| 5,143,877 | A | 9/1992 | Geus |
| 5,145,824 | A | 9/1992 | Buffum |
| 5,155,242 | A | 10/1992 | Shankar |
| 5,187,140 | A | 2/1993 | Thorsteinson et al. |
| 5,228,484 | A | 7/1993 | Johnson |
| 5,364,826 | A | 11/1994 | Kemp |
| 5,380,697 | A | 1/1995 | Matusz |
| 5,380,885 | A | 1/1995 | Kemp |
| 5,418,202 | A | 5/1995 | Evans |
| 5,447,897 | A | 9/1995 | Kemp |
| 5,486,628 | A | 1/1996 | Kemp |
| 5,519,152 | A | 5/1996 | Gorcester |
| 5,545,603 | A | 8/1996 | Kemp |
| 5,597,773 | A | 1/1997 | Evans |
| 5,663,385 | A | 9/1997 | Kemp |
| 5,703,253 | A | 12/1997 | Evans |
| 5,719,299 | A | 2/1998 | Raa |
| 5,739,075 | A | 4/1998 | Matusz |
| 5,780,657 | A | 7/1998 | Cooker et al. |
| 5,801,259 | A | 9/1998 | Kowaleski |
| 5,840,932 | A | 11/1998 | Evans |
| 5,874,653 | A | 2/1999 | Van Kruchten |
| 5,929,259 | A | 7/1999 | Lockemeyer |
| 6,843,907 | B1 | 1/2005 | Kanazirev et al. |
| 2004/0014999 | A1 | 1/2004 | Chipman et al. |
| 2004/0198993 | A1 | 10/2004 | Matusz |
| 2006/0009647 | A1 | 1/2006 | Yeates et al. |
| 2009/0069583 | A1 | 3/2009 | Rizkalla et al. |

FOREIGN PATENT DOCUMENTS

| | | |
|---|---|---|
| CN | 1041591 C | 1/1999 |
| EP | 0266015 A1 | 5/1988 |
| EP | 0324224 A1 | 7/1989 |
| EP | 0352850 A1 | 1/1990 |
| EP | 0357293 A1 | 3/1990 |
| EP | 0352850 B1 | 1/1994 |
| EP | 1458699 B1 | 11/2005 |
| GB | 1411315 | 10/1975 |
| WO | 0183105 A1 | 11/2001 |
| WO | 0196324 A2 | 12/2001 |
| WO | 03044002 A1 | 5/2003 |
| WO | 2004002972 A2 | 1/2004 |
| WO | 2004092148 A2 | 10/2004 |
| WO | 2005035513 A1 | 4/2005 |
| WO | 2008144396 A2 | 11/2008 |
| WO | 2008144402 A2 | 11/2008 |
| WO | 2008144409 A2 | 11/2008 |

OTHER PUBLICATIONS

Yeung, King Lun, et al., "Effects of 1,2 Dichloroethane Addition on the Optimal Silver Catalyst Distribution in Pellets for Epoxidation of Ethylene". Journal of Catalysis 174, pp. 1-12, Article No. CA971890 (1998).

Endo, Osamu, et al., "The Effect of a Water Overlayer on the Chlorine-Chemisorbed Ag(100) Surface Studied by CL K-edge X-ray Absorption Fine Structure." Surface Science 463, pp. 135-144, (2000).

Sinopec Tech, "S Zorb, Sulfur Removal Technology". Sinopec Tech, fact sheet (2009).

Engelhard Corp., "Sulfur Removal Technology, Zinc Oxide Adsorbent for Feedstock Purification". Englehard Corp. fact sheet. (2005).

Alptekin, Gökhan O., Ph.D., "Sorbents for Desulfurization of Hydrocarbon Fuels (Natural Gas, LPG and Jet Fuel) for Fuel Cell Applications." PowerPoint presentation. (Oct. 12, 2006).

Velu, S., et al. "Selective Adsorption for Removing Sulfur from Jet Fuel Over Zeolite-Based Adsorbents." Ind. Eng. Chem. Res., vol. 42, No. 21, pp. 5293-5304, (2003).

Grutzeck, Michael, "SO2 Removal from Flue Gases Using Utility Synthesized Zeolites." 4th Semi-Annual Report (96210R04), Materials Research Laboratory, Pennsylvania State University. (Oct. 31, 1998).

International Search Report for PCT/US2010/061549 Written Opinion of the International Searching Authority for PCT/US2010/061549.

International Search Report for PCT/US2010/031673 Written Opinion of the International Searching Authority for PCT/US2010/031673.

International Search Report for PCT/US2010/031533 Written Opinion of the International Searching Authority for PCT/US2010/031533.

International Search Report for PCT/US2010/031668 Written Opinion of the International Searching Authority for PCT/US2010/031668.

J.M. Berty; "Ethylene Oxide Synthesis." (Applied Industrial Catalysts, vol. 1, pp. 207-238, Academic Press (1983).

J.M. Berty;"Inhibitor Action of chlorinated Hydrocarbons in Oxidation of Ethylene Oxide." (Chem. Eng. Comm. vol. 82 pp. 229-232, Gordon and Breach Science Publishers S.A. (1989).

R. Aaron Edit; "Targeted Signal Enhancement (TSE); A Powerful Means of Boosting Process GC Detection Limits by1-2 Orders of Magnitude." (Presented at IFPAC 2007, Baltimore, MD, Dow Chemical Canada Inc.

J.P. Durand, A. Rokicki; "Effect of {S} in the Feed on Performance of Commercial EO Catalysts." (Abstract) 22nd North American Catalysts Society Meeting. (Jun. 5-10, 2011).

English and Japanese translations of "Mechanism of talyst Deterioration and Prevention Measures Thereof", pp. 173-1864 (Mar. 23, 1995).

English and Japanese translations of "History and Future Perspective of Development of Practical Use of Silver Catalyst", Catalysis Society of Japan, vol. 38, No. 3, pp. 212-216 (1996).

English and Japanese translations f "Chemical Process (Basic to Developing Technology)", ed. Kagakukogakukai, pp. 118-119 (1998).

English and Japanese translations of "Petrochemical Industry Handbook", pp. 124-131, 1962.

English and Japanese translations of "Petrotech", vol. 20, No. 3, pp. 248-251 (1997).

\* cited by examiner

METHOD OF CONTROLLING THE PRODUCTION OF SILVER CHLORIDE ON A SILVER CATALYST IN THE PRODUCTION OF ALKYLENE OXIDES

CROSS-REFERENCE TO RELATED APPLICATIONS

This application claims the benefit of U.S. Provisional Application No. 61/290,357, filed Dec. 28, 2009, the entirety of which is hereby incorporated by reference.

TECHNICAL FIELD

This disclosure relates generally to processes for making alkylene oxides, and more specifically, to a method of reducing the formation of silver chloride on a silver catalyst used in the production of alkylene oxides.

BACKGROUND

Alkylene oxides are known for a multiplicity of utilities. Ethylene oxide, for example, is used to produce ethylene glycol, which is used as an automotive coolant, as antifreeze, and in preparing polyester fibers and resins, nonionic surfactants, glycol ethers, ethanolamines, and polyethylene polyether polyols. Propylene oxide is used to produce propylene glycol and polypropylene polyether polyols, which are used in polyurethane polymer applications.

The production of alkylene oxides via catalytic epoxidation of olefins in the presence of oxygen using silver based catalysts is known. Conventional silver-based catalysts used in such processes typically provide a relatively lower efficiency or "selectivity" (i.e., a lower percentage of the reacted alkylene is converted to the desired alkylene oxide). In certain exemplary processes, when using conventional catalysts in the epoxidation of ethylene, the theoretically maximal efficiency towards ethylene oxide, expressed as a fraction of the ethylene converted, does not reach values above the 6/7 or 85.7 percent limit. Therefore, this limit had long been considered to be the theoretically maximal efficiency of this reaction, based on the stoichiometry of the following reaction equation:

$$7C_2H_4 + 6O_2 \rightarrow 6C_2H_4O + 2CO_2 + 2H_2O$$

cf. Kirk-Othmer's Encyclopedia of Chemical Technology, 4th ed., Vol. No. 9, 1994, p. 926.

Certain "high efficiency" or "high selectivity" modern silver-based catalysts are highly selective towards alkylene oxide production. For example, when using certain modern catalysts in the epoxidation of ethylene, the theoretically maximal efficiency towards ethylene oxide can reach values above the 6/7 or 85.7 percent limit referred to, for example 88 percent or 89 percent, or above. As used herein, the terms "high efficiency catalyst" and "high selectivity catalyst" refer to a catalyst that is capable of producing an alkylene oxide from the corresponding alkylene and oxygen at an efficiency greater than 85.7 percent. The observed actual efficiency of a high efficiency catalyst may fall below 85.7 percent under certain conditions based on process variables, catalyst age, etc. However, if the catalyst is capable of achieving at least an 85.7 percent efficiency, it is considered to be a high efficiency catalyst. Such highly efficient catalysts, which may comprise as their active components silver, rhenium, at least one further metal, and optionally, a rhenium co-promoter, are disclosed in EP0352850B1 and in several subsequent patent publications. As used herein the term "promoter" refers to a material that increases the efficiency of a reaction for a particular product. "Promoters," sometimes referred to as "inhibitors" or "moderators," refer to materials that enhance the performance of the catalysts by either increasing the rate towards the desired formation of alkylene oxide and/or suppressing the undesirable oxidation of olefin or alkylene oxide to carbon dioxide and water, relative to the desired formation of alkylene oxide. As used herein, the term "co-promoter" refers to a material that—when combined with a promoter—increases the promoting effect of the promoter. In addition, promoters may also be referred to as "dopants." In the case of those promoters that provide high efficiencies, the terms "high efficiency dopants" or "high selectivity dopants" may be used.

"Promoters" can be materials that are introduced to catalysts during the preparation of the catalysts (solid phase promoters). In addition, "promoters" can also be gaseous materials that are introduced to the epoxidation reactor feed (gas phase promoters). In one example, an organic halide gas phase promoter may be added continuously to the epoxidation reactor feed to increase the catalyst efficiency. For silver-based ethylene epoxidation catalysts, both solid and gas phase promoters are typically required in any commercial processes.

All silver based catalysts used in alkylene oxide production processes are subject to an aging-related performance decline during normal operation, and they need to be exchanged periodically. The aging manifests itself by a reduction in the activity of the catalyst and may also manifest itself by a reduction in efficiency. Usually, when a reduction in catalyst activity occurs, the reactor temperature is increased in order to maintain a constant alkylene oxide production rate. The reactor temperature may be increased until it reaches the design limit or becomes undesirably high, or the efficiency may become undesirably low, at which point in time the catalyst is deemed to be at the end of its lifetime and would need to be exchanged or regenerated. Current industry practice is to discharge and replace the catalyst when it is at the end of its useful life. The silver is recovered and promoters may be recovered from the discharged catalyst.

The optimal quantity of the gas phase promoter depends on the reaction conditions and on the type of catalyst used. Conventional catalysts have relatively flat efficiency curves with respect to the gas phase promoter concentration in the feed, i.e., the efficiency is almost invariant (i.e., the change in efficiency with respect to a change in gas phase promoter concentration in the feed is less than about 0.1%/ppm) over a wide range of promoter concentrations, and this invariance is substantially unaltered as reactor temperature is changed (i.e., the change in efficiency with respect to a change in reactor temperature is less than about 0.1%/° C.) during prolonged operation of the catalyst. However, conventional catalysts have nearly linear activity decline curves with respect to the gas phase promoter concentration in the feed, i.e., with increasing gas phase promoter concentration in the feed, temperature has to be increased or the alkylene oxide production rate will be reduced. Therefore, when using a conventional catalyst, for optimum efficiency, the gas phase promoter concentration in the feed can be chosen at a level at which the maximum efficiency can be maintained at relatively lower operating temperatures. Typically, the gas phase promoter concentration in the feed can remain substantially the same during the entire lifetime of a conventional catalyst. Alternatively, the reactor temperature may be adjusted to obtain a desired production rate without any substantial impact on efficiency.

By contrast, high efficiency catalysts tend to exhibit relatively steep efficiency curves as a function of gas phase promoter concentration as the concentration moves away from the value that provides the highest efficiency (i.e., the change in efficiency with respect to a change in gas phase promoter concentration is at least about 0.2%/ppm when operating away from the efficiency maximizing promoter concentration). Thus, small changes in the promoter concentration can result in significant efficiency changes. The efficiency also exhibits a pronounced maximum, i.e., an optimum, at certain concentrations (or feed rates) of the gas phase promoter, when reactor pressure and feed gas composition are kept unchanged for a given reaction temperature and catalyst age. Moreover, the efficiency curves and the optimum gas phase promoter concentration tend to be strong functions of reactor temperature and are thus significantly affected if reactor temperature is varied, for example, to compensate for decreases in catalyst activity (i.e., the change in efficiency with respect to a change in reactor temperature can be at least about 0.1%/° C. when operating away from the efficiency maximizing promoter concentrations for the selected temperatures). In addition, high efficiency catalysts have exhibited significant activity increases with increases in the gas phase promoter concentration in the feed, i.e., with increasing gas phase promoter concentration in the feed, temperature has to be decreased or the production rate will increase.

It has been found that under certain circumstances, silver chloride tends to irreversibly form on high-efficiency silver catalysts, causing a decline in activity and requiring more frequent catalyst replacement. While the formation of silver chloride might be expected to occur due to the addition of organic chloride promoters, in some cases the level of silver chloride formation is even greater than would normally be expected from operation with the given organic chloride promoter concentrations. Thus, a need has arisen for a process of making alkylene oxides which addresses the foregoing issues.

SUMMARY

In accordance with one aspect, a process for controlling the formation of silver chloride on a high-efficiency silver catalyst used in the production of an alkylene oxide from a reactor feed gas comprising an alkylene, oxygen, and at least one organic chloride is provided. The process comprises controlling the concentration of sulfur in the reactor feed gas on an atomic basis to no more than about 50 parts per billion (volume). Reactor feed gas sulfur concentrations of no more than about 40 ppbv are preferred, and concentrations of no more than about 30 ppbv are even more preferred. Sulfur concentrations of no more than about 20 ppbv are still more preferred. Sulfur concentrations of no more than about 10 ppbv are yet more preferred, and sulfur concentrations of no more than about 5 ppbv are further preferred. In certain especially preferred embodiments, the reactor feed gas sulfur concentration on an atomic basis is no more than about 1 ppbv. In certain exemplary embodiments, the step of controlling the concentration of sulfur in the reactor feed gas comprises selectively fluidly coupling at least one alkylene feed gas source to the process. In accordance with other examples, the step of controlling the concentration of sulfur in the reactor feed gas comprises desulfurizing an alkylene feed and/or ballast gas containing sulfur-compounds.

In accordance with another aspect, a process for manufacturing an alkylene oxide is provided. The process comprises providing an alkylene feed comprising at least one sulfur-containing compound, removing at least a portion of the at least one sulfur-containing compound from the alkylene feed to yield a desulfurized alkylene feed, combining the desulfurized alkylene feed with at least oxygen and at least one organic chloride to yield a reactor feed gas having a concentration of sulfur (on an atomic basis) of no more than about 50 ppbv, and reacting the reactor feed gas over a high-efficiency silver catalyst to yield a reaction product comprising the alkylene oxide. In certain examples, the step of removing at least a portion of the at least one sulfur-containing compound from the alkylene feed comprises adsorbing the at least a portion of the at least one sulfur-containing compound on an adsorbent bed. In other examples, the process further comprises adjusting the adsorbent bed temperature to control the concentration of sulfur in the reactor feed gas. In further examples, the step of removing at least a portion of the at least one sulfur-containing compound from the alkylene feed comprises converting the at least a portion of the at least one sulfur-containing compound to hydrogen sulfide and adsorbing at least a portion of the hydrogen sulfide on the adsorbent bed. In additional examples, the step of removing at least a portion of the at least one sulfur-containing compound from the alkylene feed comprises scrubbing the alkylene feed with a basic compound.

In accordance with a further aspect, an alkylene oxide plant is provided which comprises a desulfurizing unit and an alkylene oxide reactor. The desulfurizing unit has an alkylene feed gas inlet and a desulfurized alkylene gas outlet. The alkylene oxide reactor comprises a high-efficiency silver catalyst bed, a desulfurized reactor feed gas inlet, and an alkylene oxide product outlet, wherein the desulfurized reactor feed gas inlet is fluidly coupled to the desulfurized alkylene gas outlet of the desulfurizing unit, an oxygen source, and an organic chloride source. The plant is configured to produce a reactor feed having a sulfur concentration on an atomic basis of no more than about 50 ppbv. In certain embodiments, the desulfurizing unit comprises a sulfur conversion unit fluidly coupled to a hydrogen sulfide adsorbent bed, the sulfur conversion unit comprises the alkylene feed gas inlet, and the hydrogen sulfide adsorbent bed comprises the desulfurized alkylene gas outlet. In additional examples, the alkylene oxide plant further comprises a heavy hydrocarbon contaminant pretreater comprising a heavy-hydrocarbon contaminated alkylene feed inlet and a decontaminated alkylene product outlet, wherein the decontaminated alkylene product outlet is fluidly coupled to the alkylene feed gas inlet of the desulfurizing unit.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are exemplary and are not intended to be exhaustive or otherwise limit or restrict the claims to the precise forms and configurations shown in the drawings and disclosed in the following detailed description.

DETAILED DESCRIPTION

Figure 1:
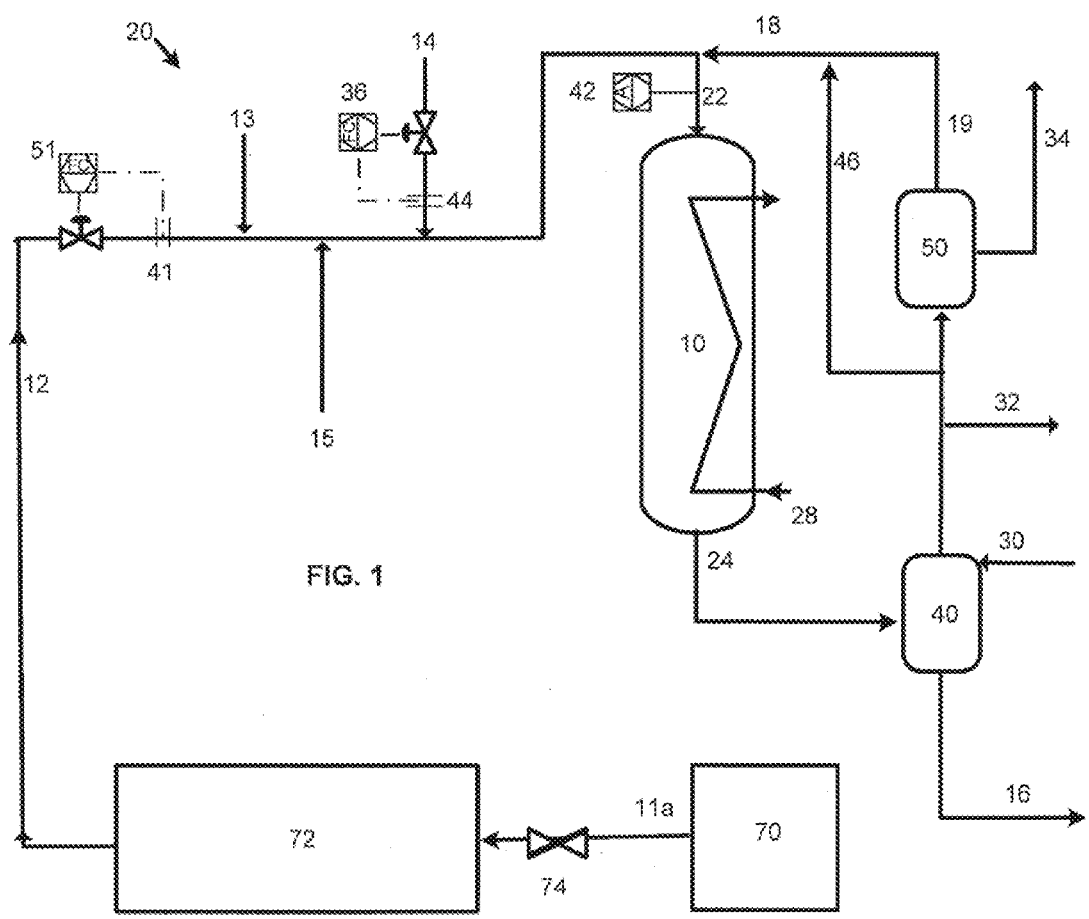
FIG. 1 is a process flow diagram depicting an embodiment of a process for making an alkylene oxide by epoxidizing an olefin which includes a desulfurizing unit.

As discussed below, the present disclosure provides a method of reducing the formation of silver chloride on a high efficiency silver catalyst used to make an alkylene oxide. The process of making the alkylene oxide comprises reacting the corresponding alkylene with oxygen in the presence of an organic chloride gas phase promoter. The method exploits the unexpected discovery that the concentration of sulfur in an alkylene oxide reactor feed gas affects the formation of silver chloride. Thus, the process involves controlling the concentration of sulfur, on an equimolar sulfur atom basis, in the reactor feed gas.

In order to facilitate an understanding of the present disclosure, it is useful to define certain terms relating to catalyst and process performance. The "activity" of a catalyst in a fixed bed reactor is generally defined as the reaction rate towards the desired product per unit of catalyst volume in the reactor. The activity relates to both the total number of available active sites and the reaction rate of each site. The number of active sites can be reduced in several ways. For example, they can be reduced by coalescence of the silver particles, which reduces the surface area of the silver available for reaction. They can also be reduced by poisoning, for example by reaction with trace sulfur compounds in the reactor feed. The number of active sites can also be reduced by reaction with normal process constituents, such as by reaction with chloride compounds in the process stream to form silver chloride compounds, which are inactive towards the epoxidation reaction. The activity will also decline if the reaction rate goes down for at least some of the active sites (e.g., due to localized poisoning) independent of the total number of active sites. To compensate for the activity decline in order to maintain a given production rate, certain reaction conditions have to be changed to increase the overall production rate of the available active sites. For instance, reaction temperature is often raised to provide more energy to the active sites for this purpose. "Activity" can be quantified in a number of ways, one being the mole percent of alkylene oxide contained in the outlet stream of the reactor relative to that in the inlet stream (the mole percent of alkylene oxide in the inlet stream typically, but not necessarily, approaches zero percent) while the reactor temperature is maintained substantially constant; and another being the temperature required to maintain a given rate of alkylene oxide production. In many instances, activity is measured over a period of time in terms of the mole percent of alkylene oxide produced at a specified constant temperature. Alternatively, activity may be measured as a function of the temperature required to sustain production of a specified constant mole percent of alkylene oxide, such as ethylene oxide, given other conditions such as pressure and total moles in the feed.

The "efficiency" of the epoxidation, which is synonymous with "selectivity," refers to the relative amount (as a fraction or in percent) of converted or reacted olefin that forms a particular product. For example, the "efficiency to alkylene oxide" refers to the percentage on a molar basis of converted or reacted olefin that forms alkylene oxide. One measure of the useful life of a catalyst is the length of time that reactants can be passed through the reaction system during which time acceptable productivity is obtained in light of all relevant factors. The "yield" of alkylene oxide refers to the net number of moles of alkylene oxide produced by the process divided by the net number of moles of olefin fed to the process for any given time period.

FIG. 1 illustrates a process 20 for making an alkylene oxide. Process 20 includes a reactor 10 comprising a tubular vessel with a catalyst bed disposed in it. Olefin (i.e., alkylene) feed stream 12 (which may also include saturated hydrocarbons, such as ethane, as an impurity) is combined with ballast gas 13, oxygen feed 15 and gas phase promoter feed 14 to define reactor feed stream 22 proximate the reactor inlet. Reactor product stream 24 includes the alkylene oxide ("AO") product, plus side products (e.g., $CO_2$, $H_2O$, and small amounts of saturated hydrocarbons), unreacted olefin, oxygen, and inerts. Water stream 30 is added to alkylene oxide absorber 40 to absorb alkylene oxide product from reactor product stream 24. Net product stream 16 comprises water and alkylene oxide, and the alkylene oxide is subsequently separated from the water.

If desired, recycle stream 18 may also be provided to reduce the amount of unreacted olefin in the net product stream 16. One example of a suitable recycle system is depicted in FIG. 1. As shown in the figure, alkylene oxide absorber 40 produces an overhead gas stream comprising unreacted olefin, saturated hydrocarbon impurities or byproducts, and carbon dioxide. Carbon dioxide is removed in $CO_2$ removal unit 50 (e.g., a $CO_2$ scrubber) and exits $CO_2$ removal unit 50 in carbon dioxide stream 34. The overhead stream 19 from unit 50 is combined with $CO_2$ removal unit 50 bypass stream 46 to define recycle stream 18. Recycle stream 18 is combined with olefin feed 12, ballast gas 13, oxygen feed 15, and gas phase promoter feed 14 to define reactor feed stream 22. Purge line 32 is also provided to provide for the removal of saturated hydrocarbon impurities (e.g., ethane), inerts (such as argon), and/or byproducts (as well as carbon dioxide) to prevent their accumulation in reactor feed 22.

The olefin comprising olefin feed stream 12 may be any olefin, including aromatic olefins and di-olefins, whether conjugated or not. However, preferred olefins are mono-olefins having the following formula:

wherein, $R_1$ and $R_2$ are individually selected from the group consisting of hydrogen and alkyl radicals having from 1 to 6 carbon atoms. Propylene ($R_1=CH_3$, $R_2=H$) and ethylene ($R_1=R_2=H$) are more preferred, and ethylene is most preferred. Correspondingly, preferred alkylene oxides in reactor product stream 24 are of the formula:

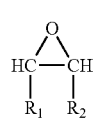

wherein, $R_1$ and $R_2$ are individually selected from the group consisting of hydrogen and alkyl radicals having from 1 to 6 carbon atoms. Propylene oxide ($R_1$=$CH_3$, $R_2$=H) and ethylene oxide ($R_1$=$R_2$=H) are more preferred, and ethylene oxide is most preferred.

Oxygen feed 15 may comprise substantially pure oxygen or a stream enriched with oxygen, such as air. If pure oxygen is used, ballast gases or diluents such as nitrogen or methane ballast stream 13 may also be included to maintain the oxygen concentration below the maximum level allowed by flammability considerations. The concentration of oxygen in reactor feed stream 22 may vary over a wide range, and in practice, flammability is generally the limiting factor for oxygen concentration. Generally, the oxygen concentration in reactor feed 22 will be at least about one (1) mole percent and preferably at least about two (2) mole percent. The oxygen concentration will generally be no more than about fifteen (15) mole percent and preferably no more than about twelve (12) mole percent. The ballast gas 13 (e.g., nitrogen or methane) is generally from about 50 mole percent to about 80 mole percent of the total composition of reactor feed stream 22. Methane ballast gas is preferred over nitrogen because, due to its higher heat capacity, it facilitates the use of higher oxygen concentrations in the cycle, and therefore, improves both activity and efficiency.

The concentration of olefin in reactor feed stream 22 may vary over a wide range. However, it is preferably at least about eighteen (18) mole percent and more preferably at least about twenty (20) mole percent. The concentration of olefin in reactor feed stream 22 is preferably no greater than about 50 mole percent, and more preferably is no greater than about 40 mole percent.

When present, the carbon dioxide concentration in reactor feed stream 22 has a large adverse effect on the efficiency, activity and/or stability of catalysts used in reactor 10. Carbon dioxide is produced as a reaction by-product and may also be introduced with other inlet reaction gases as an impurity. In commercial ethylene epoxidation processes, at least part of the carbon dioxide is removed continuously in order to control its concentration to an acceptable level in the cycle. The carbon dioxide concentration in reactor feed 22 is generally no more than about 5 mole percent, preferably no more than about 3 mole percent, and even more preferably no more than about 2 mole percent of the total composition of reactor feed 22. Water is also a reaction by-product, and may be present in the feed gases in concentrations that are preferably from 0 to no more than about three (3) mole percent.

The gas phase promoter is generally a compound that enhances the efficiency and/or activity of process 20 for producing the desired alkylene oxide. Preferred gas phase promoters include organic chlorides. More preferably, the gas phase promoter is at least one selected from the group consisting of methyl chloride, ethyl chloride, ethylene dichloride, vinyl chloride, and mixtures thereof. Ethyl chloride and ethylene dichloride are most preferred. Using chlorohydrocarbon gas phase promoters as an example, it is believed that the ability of the promoter to enhance the performance (e.g., efficiency and/or activity) of process 20 for the desired alkylene oxide depends on the extent to which the gas phase promoter chlorinates the surface of the catalyst in reactor 10, for example, by depositing particular chlorine species such as atomic chlorine or chloride ions on the catalyst or in the gas phase above the catalyst. However, hydrocarbons lacking chlorine atoms are believed to strip chlorides from the catalyst, and therefore, detract from the overall performance (e.g. efficiency and/or activity) enhancement provided by the gas phase promoter. Discussions of this phenomenon may be found in Berty, "Inhibitor Action of Chlorinated Hydrocarbons in the Oxidation of Ethylene to Ethylene Oxide," *Chemical Engineering Communications*, Vol. 82 (1989) at 229-232 and Berty, "Ethylene Oxide Synthesis," *Applied Industrial Catalysis*, Vol. I (1983) at 207-238. Paraffinic compounds, such as ethane and propane, are believed to be especially effective at stripping chlorides from the catalyst. However, olefins, such as ethylene or propylene, are also believed to act to strip chlorides from the catalyst. Some of these hydrocarbons may also be introduced as impurities in the ethylene feed 12 or may be present for other reasons (such as the use of recycle stream 18). Typically, the preferred concentration of ethane in the reactor feed 22, when present, is from 0 to about 2 mole percent. Given the competing effects of the gas phase promoter and the non-halogenated, non-promoting hydrocarbons in reactor feed stream 22, it is convenient to define an "overall catalyst chloriding effectiveness value" that represents the net effect of gas phase species in chloriding the catalyst. In the case of organic chloride gas-phase promoters, the overall catalyst chloriding effectiveness can be defined as the dimensionless quantity Z* and represented by the following formula:

$$Z^* = \frac{\text{ethyl chloride equivalent } (ppmv)}{\text{ethane equivalent (mole percent)}} \quad (1)$$

wherein the ethyl chloride equivalent is the concentration in ppmv of ethyl chloride that provides substantially the same catalyst chloriding effectiveness of the organic chlorides present in reactor feed stream 22 at the concentrations of the organic chlorides in the reactor feed stream 22; and the ethane equivalent is the concentration of ethane in mole percent that provides substantially the same catalyst dechloriding effectiveness of the non-chloride containing hydrocarbons in the reactor feed stream 22 at the concentrations of the non-chloride containing hydrocarbons in the reactor feed stream 22.

If ethyl chloride is the only gaseous chloride-containing promoter present in reactor feed stream 22, the ethyl chloride equivalent (i.e., the numerator in equation (1)) is the ethyl chloride concentration in ppmv. If other chlorine-containing promoters (specifically vinyl chloride, methyl chloride or ethylene dichloride) are used alone or in conjunction with ethyl chloride, the ethyl chloride equivalent is the concentration of ethyl chloride in ppmv plus the concentrations of the other gaseous chloride-containing promoters (corrected for their effectiveness as a promoter as compared to ethyl chloride). The relative effectiveness of a non-ethyl chloride promoter can be measured experimentally by replacing ethyl chloride with the other promoter and determining the concentration needed to obtain the same level of catalyst performance provided by ethyl chloride. As a way of further illustration, if the required concentration of ethylene dichloride at the reactor inlet is 0.5 ppmv to realize equivalent effectiveness in terms of catalyst performance provided by 1 ppmv ethyl chloride, then the ethyl chloride equivalent for 1 ppmv ethylene dichloride would be 2 ppmv ethyl chloride. For a hypothetical feed having 1 ppmv ethylene dichloride and 1 ppmv ethyl chloride, the ethyl chloride equivalent in the numerator of Z* would then be 3 ppmv. As a further example, it has been found that for certain catalysts methyl chloride has approximately 10 times less the chloriding effectiveness of ethyl chloride. Therefore, for such catalysts the ethyl chloride equivalent for a given concentration of methyl chloride in ppmv is 0.1×(methyl chloride concentration in ppmv). It has also been found that for certain catalysts, vinyl chloride has the same chloriding effectiveness as ethyl chloride. Therefore, for such catalysts the ethyl chloride equivalent for a given concentration of vinyl chloride in ppm is 1.0×(vinyl chloride concentration in ppmv). When more than two chlorine-containing promoters are present in reactor feed stream 22, which is often the case in commercial ethylene epoxidation processes, the overall ethyl chloride equivalent is the sum of the corresponding ethyl chloride equivalents for each individual chlorine-containing promoter that is present. As an example, for a hypothetical feed of 1 ppmv ethylene dichloride, 1 ppmv ethyl chloride, and 1 ppmv vinyl chloride, the ethyl chloride equivalent in the numerator of $Z^*$ would be 2*1+1+1*1=4 ppmv.

The ethane equivalent (i.e., the denominator in equation (1)) is the concentration of ethane in mole percent in reactor feed stream 22 plus the concentrations of the other hydrocarbons effective in removing chloride from the catalysts, corrected for their effectiveness for dechlorination relative to ethane. The relative effectiveness of ethylene compared to ethane can be measured experimentally by determining the inlet ethyl chloride equivalent concentration that provides the same level of catalyst performance for a feed comprising both ethylene and ethane as compared to the same feed with the same ethylene concentration but a specific ethyl chloride equivalent concentration and no ethane. As a way of further illustration, if with a feed composition comprising an ethylene concentration of 30.0 mole percent and an ethane concentration of 0.30 mole percent, a level of 6.0 ppm ethyl chloride equivalents is found to provide the same level of catalyst performance as 3.0 ppm ethyl chloride equivalents with a similar feed composition but lacking ethane, then the ethane equivalent for 30.0 mole percent ethylene would be 0.30 mole percent. For an inlet reactor feed 22 having 30.0 mole percent ethylene and 0.3 mole percent ethane, the ethane equivalent then will be 0.6 mole percent. As another illustration, it has been found that for certain catalysts methane has about 500 times less the dechloriding effectiveness of ethane. Thus, for such catalysts the ethane equivalent for methane is 0.002×(methane concentration in mol %). For a hypothetical inlet reactor feed 22 having 30.0 mole percent ethylene and 0.1 mole percent ethane, the ethane equivalent then will be 0.4 mole percent. For an inlet reactor feed 22 having 30.0 mole percent ethylene, 50 mole percent methane, and 0.1 mole percent ethane, the ethane equivalent then will be 0.5 mole percent. The relative effectiveness of hydrocarbons other than ethane and ethylene can be measured experimentally by determining the inlet ethyl chloride equivalent concentrations required to achieve the same catalyst performance for a feed comprising the hydrocarbon of interest in the feed at two different concentrations of ethane in the feed. If a hydrocarbon compound is found to have a very small dechloriding effect and is also present in low concentrations, then its contribution to the ethane equivalent concentration in the $Z^*$ calculation may be negligible, and it may be omitted from the calculation.

Thus, given the foregoing relationships, in the case where reactor feed stream 22 includes ethylene, ethyl chloride, ethylene dichloride, vinyl chloride, and/or ethane, the overall catalyst chloriding effectiveness value of process 20 can be defined as follows:

$$Z^* = \frac{(ECL + 2^*EDC + VCL)}{(C_2H_6 + 0.01^*C_2H_4)} \qquad (2)$$

wherein ECL, EDC, and VCL are the concentrations in ppmv of ethyl chloride ($C_2H_5Cl$), ethylene dichloride (Cl—$CH_2$—$CH_2$—Cl), and vinyl chloride ($H_2C=CH$—Cl), respectively, in reactor feed stream 22. $C_2H_6$ and $C_2H_4$ are the concentrations in mole percent of ethane and ethylene, respectively, in reactor feed stream 22. It is important that the relative effectiveness of the gaseous chlorine-containing promoter and the hydrocarbon dechlorinating species also be measured under the reaction conditions which are being used in the process. $Z^*$ will preferably be maintained at a level that is no greater than about 20 and which is most preferably no greater than about 15. $Z^*$ is preferably at least about 1.

Although the gaseous chlorine-containing promoter may be supplied as a single species, upon contact with the catalyst, other species may be formed leading to a mixture in the gas phase. Consequently, if the reaction gases are recycled such as via recycle stream 18, a mixture of species will be found in the inlet of the reactor. In particular, the recycled reaction gases at the inlet may contain ethyl chloride, vinyl chloride, ethylene dichloride and or methyl chloride, even though only ethyl chloride or ethylene dichloride is supplied to the system. The concentrations of ethyl chloride, vinyl chloride, and ethylene dichloride must be considered in calculating $Z^*$.

The order in which the inlet gases (alkylene and oxygen and ballast gas) and gas phase promoter are mixed together is not critical, and they may be mixed simultaneously or sequentially. The order of mixing of the gaseous components of the process may be chosen for convenience and/or for safety reasons. For example, oxygen is generally added after the ballast gas for reasons of safety. However, the gas phase promoter should be present in reactor feed stream 22 as it is introduced to the solid catalyst in reactor 10.

In the embodiment of FIG. 1, Reactor 10 is a fixed bed reactor. However, any suitable reactor may be used, for example, fixed bed tubular reactors, continuous stirred tank reactors (CSTR), and fluid bed reactors, a wide variety of which are well known to those skilled in the art and need not be described in detail herein. The desirability of recycling unreacted feed, or employing a single-pass system, or using successive reactions to increase ethylene conversion by employing reactors in series arrangement can also be readily determined by those skilled in the art. The particular mode of operation selected is usually dictated by process economics. The epoxidation reaction is generally exothermic. Thus, a coolant system 28 (e.g., a cooling jacket or a hydraulic circuit with a coolant fluid such as a heat transfer fluid or boiling water) is provided to regulate the temperature of reactor 10. The heat transfer fluid can be any of several well-known heat transfer fluids, such as tetralin (1,2,3,4-Tetrahydronaphthalene). In reactors cooled with boiling water, the coolant is introduced to the cooling side of the reactor, most commonly the shell side, as liquid water. As it flows through the cooling side, the water removes heat from the process side, and some of the water is vaporized to steam. The coolant exits the cooling side of the reactor as a mixture of water and steam. The steam exiting the reactor is condensed by removing heat from it, and is recycled back to the inlet of the coolant side. The temperature of the coolant in the reactor is determined by the boiling point of the water, which in turn is determined by the pressure under which it operates. The pressure is controlled by means of a vent valve which vents off some pressure from the steam-water mixture exiting the cooling side of the reactor. Typically, a closed-loop controller is used to regulate the coolant temperature by automatically adjusting the vent valve to maintain the pressure necessary to maintain the desired temperature. The epoxidation reaction is carried out at a temperature that is preferably at least about 200° C., more preferably at least about 210° C., and most preferably at least about 220° C. Reactor temperatures of no more than 300° C. are preferred, and reactor temperatures of no more than about 290° C. are more preferred. Reactor temperatures of no more than about 280° C. are most preferred. The reactor pressure is selected based on the desired mass velocity and productivity and ranges generally from about 5 atm (506 kPa) to about 30 atm (3.0 MPa). The gas hourly space velocity (GHSV) is preferably greater than about 3000 $h^{-1}$, more preferably greater than about 4,000 $hr^{-1}$, and most preferably greater than about 5,000 $hr^{-1}$.

Reactor 10 includes a high efficiency, silver catalyst. Generally, the highly efficient silver based catalyst is a supported catalyst. The support (also known as a "carrier") may be selected from a wide range of inert support materials. Such support materials may be natural or artificial inorganic materials and they include silicon carbide, clays, pumice, zeolites, charcoal and alkaline earth metal carbonates, such as calcium carbonate. Preferred are refractory support materials, such as alumina, magnesia, zirconia and silica. The most preferred support material is α-alumina. In one exemplary embodiment, silver is deposited on the catalyst carrier as are one or more solid promoters, which are discussed further below.

There are many well-known methods of preparing supports suitable for use in ethylene oxide catalysts. Some of such methods are described in, for example, U.S. Pat. Nos. 4,379,134; 4,806,518; 5,063,195; 5,384,302, U.S. Patent Application 20030162655 and the like. For example, an alpha-alumina support of at least 95% purity can be prepared by compounding (mixing) the raw materials, extrusion, drying and a high temperature calcination. In this case, the starting raw materials usually include one or more alpha-alumina powder(s) with different properties, a clay-type material which may be added as binder to provide physical strength, and a burnout material (usually an organic compound) used in the mix to provide desired porosity after its removal during the calcination step. The levels of impurities in the finished carrier are determined by the purity of the raw materials used, and their degree of volatilization during the calcination step. Common impurities may include silica, alkali and alkaline earth metal oxides and trace amounts of metal and/or non-metal-containing additives. Another method for preparing a carrier having particularly suitable properties for ethylene oxide catalyst usage comprises optionally mixing zirconium silicate with boehmite alumina (AlOOH) and/or gamma-alumina, peptizing the aluminas with a mixture containing an acidic component and halide anions (preferably fluoride anions) to provide peptized halogenated alumina, forming (for example, by extruding or pressing) the peptized halogenated alumina to provide formed peptized halogenated alumina, drying the formed peptized halogenated alumina to provide dried formed alumina, and calcining the dried formed alumina to provide pills of optionally modified alpha-alumina carrier.

There have been employed alumina which has a very high purity, that is, at least 98 wt. % alpha-alumina, any remaining components being silica, alkali metal oxides (for example, sodium oxide) and trace amounts of other metal-containing and/or non-metal-containing additives or impurities. Likewise, there have been employed alumina of lower purity, that is, about 80 wt. % alpha-alumina, the balance being one or more of amorphous and/or crystalline alumina and other alumina oxides, silica, silica alumina, mullite, various alkali metal oxides (for example, potassium oxide and cesium oxide), alkaline earth metal oxides, transition metal oxides (for example, iron oxide and titanium oxide), and other metal and non-metal oxides. In addition, the material used to make the carrier may comprise compounds which have been known for improving catalyst performance, for example, rhenium, (such as rhenates) and molybdenum.

In an especially preferred embodiment, the support material comprises at least about 80 weight percent α-alumina and less than about 30 parts per million acid-leachable alkali metals by weight, the weight percent of the α-alumina and the concentration of the acid-leachable alkali metals being calculated on the weight of the carrier, where the acid-leachable alkali metals are selected from lithium, sodium, potassium, and mixtures thereof.

The alpha-alumina carrier prepared as described hereinabove preferably has a specific surface area of at least about 0.5 $m^2$/g, and more preferably, at least about 0.7 $m^2$/g. The surface area is typically less than about 10 $m^2$/g, and preferably, less than about 5 $m^2$/g. The alpha-alumina carrier preferably has a pore volume of at least about 0.3 $cm^3$/g, and more preferably, from about 0.4 $cm^3$/g to about 1.0 $cm^3$/g and a median pore diameter from about 1 to about 50 microns. A variety of carrier morphologies may be used, including pills, cylinders, cylinders with one or more longitudinal axial openings, chunks, tablets, pieces, pellets, rings, spheres, wagon wheels, saddle rings and toroids having star shaped inner and/or outer surfaces. In a preferred embodiment, the high-purity alpha-alumina preferably includes particles many of which have at least one substantially flat major surface, and having a lamellate or platelet morphology. In a more preferred embodiment the particles approximate the shape of a hexagonal plate (some particles having two or more flat surfaces), at least 50 percent of which (by number) have a major dimension of less than about 50 microns. In a preferred embodiment, the alpha-alumina carrier comprises zirconium silicate (zircon), present substantially as zirconium silicate in the finished carrier, more preferably, in an amount up to about 4 weight percent, calculated on the weight of the carrier.

Catalysts of this invention for the production of alkylene oxide, for example, ethylene oxide or propylene oxide may be prepared with the aforementioned carriers by impregnating the carrier with a solution of one or more silver compounds, depositing the silver throughout the pores of the carrier and reducing the silver compound as is well known in the art. See for example, Liu, et al., U.S. Pat. No. 6,511,938 and Thorsteinson et al., U.S. Pat. No. 5,187,140, incorporated herein by reference.

Generally, the carrier is impregnated with a catalytic amount of silver, which is any amount of silver capable of catalyzing the direct oxidation of the alkylene with oxygen or an oxygen-containing gas to the corresponding alkylene oxide. In making such a catalyst, the carrier is typically impregnated (one or more times) with one or more silver compound solutions sufficient to allow the silver to be supported on the carrier in an amount greater than about 5 percent, greater than about 10 percent, greater than about 15 percent, greater than about 20 percent, greater than about 25 percent, preferably, greater than about 27 percent, and more preferably, greater than about 30 percent by weight, based on the weight of the catalyst. Typically, the amount of silver supported on the carrier is less than about 70 percent, and more preferably, less than about 50 percent by weight, based on the weight of the catalyst.

Although silver particle size in the finished catalyst is important, the preferred range is not narrow. A suitable silver particle size can be in the range of from about 10 to about 10,000 angstroms in diameter. A preferred silver particle size ranges from greater than about 100 to less than about 5,000 angstroms in diameter. It is desirable that the silver be relatively uniformly dispersed within, throughout, and/or on the alumina carrier.

As is known to those skilled in the art, there are a variety of known promoters, that is, materials which, when present in combination with particular catalytic materials, for example, silver, benefit one or more aspect of catalyst performance or otherwise act to promote the catalyst's ability to make a desired product, for example ethylene oxide or propylene oxide. Such promoters in themselves are generally not considered catalytic materials. The presence of such promoters in the catalyst has been shown to contribute to one or more beneficial effects on the catalyst performance, for example enhancing the rate or amount of production of desired product, reducing the temperature required to achieve a suitable rate of reaction, reducing the rates or amounts of undesired reactions, etc. Competing reactions occur simultaneously in the reactor, and a critical factor in determining the effectiveness of the overall process is the measure of control one has over these competing reactions. A material which is termed a promoter of a desired reaction can be an inhibitor of another reaction, for example a combustion reaction. What is significant is that the effect of the promoter on the overall reaction is favorable to the efficient production of the desired product, for example ethylene oxide. The concentration of the one or more promoters present in the catalyst may vary over a wide range depending on the desired effect on catalyst performance, the other components of a particular catalyst, the physical and chemical characteristics of the carrier, and the epoxidation reaction conditions.

There are at least two types of promoters—solid promoters and gaseous promoters. The solid and/or gaseous promoters are provided in a promoting amount. A "promoting amount" of a certain component of a catalyst refers to an amount of that component that works effectively to provide an improvement in one or more of the catalytic properties of that catalyst when compared to a catalyst not containing said component. Examples of catalytic properties include, inter alia, operability (resistance to run-away), efficiency, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced efficiency at one set of operating conditions may be operated at a different set of conditions wherein the improvement shows up in the activity rather than the efficiency and an operator of an ethylene oxide plant will intentionally change the operating conditions in order to take advantage of certain catalytic properties even at the expense of other catalytic properties in order to maximize profits by taking into account feedstock costs, energy costs, by-product removal costs and the like.

The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

Examples of well-known solid promoters for catalysts used to produce ethylene oxide include compounds of potassium, rubidium, cesium, rhenium, sulfur, manganese, molybdenum, and tungsten. During the reaction to make ethylene oxide, the specific form of the promoter on the catalyst may be unknown. Examples of solid promoter compositions and their characteristics as well as methods for incorporating the promoters as part of the catalyst are described in Thorsteinson et al., U.S. Pat. No. 5,187,140, particularly at columns 11 through 15, Liu, et al., U.S. Pat. No. 6,511,938, Chou et al., U.S. Pat. No. 5,504,053, Soo, et al., U.S. Pat. No. 5,102,848, Bhasin, et al., U.S. Pat. Nos. 4,916,243, 4,908,343, and 5,059,481, and Lauritzen, U.S. Pat. Nos. 4,761,394, 4,766,105, 4,808,738, 4,820,675, and 4,833,261, all incorporated herein by reference. The solid promoters are generally added as chemical compounds to the catalyst prior to its use. As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions when added as a compound to the catalyst. Once in the catalyst, the form of the promoter is not always known, and the promoter may be present without the counterion added during the preparation of the catalyst. For example, a catalyst made with cesium hydroxide may be analyzed to contain cesium but not hydroxide in the finished catalyst. Likewise, compounds such as alkali metal oxide, for example cesium oxide, or transition metal oxides, for example $MoO_3$, while not being ionic, may convert to ionic compounds during catalyst preparation or in use. For the sake of ease of understanding, the solid promoters will be referred to in terms of cations and anions regardless of their form in the catalyst under reaction conditions.

The catalyst prepared on the carrier may contain alkali metal and/or alkaline earth metal as cation promoters. Exemplary of the alkali metal and/or alkaline earth metals are lithium, sodium, potassium, rubidium, cesium, beryllium, magnesium, calcium, strontium and barium. Other cation promoters include Group 3b metal ions including lanthanide series metals. In some instances, the promoter comprises a mixture of cations, for example cesium and at least one other alkali metal, to obtain a synergistic efficiency enhancement as described in U.S. Pat. No. 4,916,243, herein incorporated by reference. Note that references to the Periodic Table herein shall be to that as published by the Chemical Rubber Company, Cleveland, Ohio, in CRC Handbook of Chemistry and Physics, 46th Edition, inside back cover.

The preferred ranges of the concentration of the alkali metal promoters in the finished catalyst are not narrow and may vary over a wide range. The optimum alkali metal promoter concentration for a particular catalyst will be dependent upon performance characteristics, such as catalyst efficiency, rate of catalyst aging and reaction temperature.

The concentration of alkali metal (based on the weight of cation, for example cesium) in the finished catalyst may vary from about 0.0005 to 1.0 wt. %, preferably from about 0.005 to 0.5 wt. %. The preferred amount of cation promoter deposited on or present on the surface of the carrier or catalyst generally lies between about 10 and about 4000, preferably about 15 and about 3000, and more preferably between about 20 and about 2500 ppm by weight of cation calculated on the total carrier material. Cation promoter amounts between about 50 and about 2000 ppm by weight of the total carrier material are frequently most preferable. When the alkali metal cesium cation is used in mixture with other cations, the ratio of cesium to any other alkali metal and alkaline earth metal cation(s), if used, to achieve desired performance is not narrow and may vary over a wide range. The weight ratio of cesium to the other cation promoters may vary from about 0.0001:1 to 10,000:1, preferably from about 0.001:1 to 1,000:1.

Examples of some of the anion promoters which may be employed with the present invention include the halides, for example fluorides and chlorides, and the oxyanions of the elements other than oxygen having an atomic number of 5 to 83 of Groups 3b to 7b and 3a to 7a of the Periodic Table. One or more of the oxyanions of nitrogen, sulfur, manganese, tantalum, molybdenum, tungsten and rhenium may be preferred for some applications.

The types of anion promoters or modifiers suitable for use in the catalysts of this invention comprise, by way of example only, oxyanions such as sulfate, $SO_4^{2-}$, phosphates, for example, $PO_4^{3-}$, titanates, e.g., $TiO_3^{-2}$, tantalates, for example, $Ta_2O_6^{-2}$, molybdates, for example, $MoO_4^{-2}$, vanadates, for example, $V_2O_4^{-2}$, chromates, for example, $CrO_4^{-2}$, zirconates, for example, $ZrO_3^{-2}$, polyphosphates, manganates, nitrates, chlorates, bromates, borates, silicates, carbonates, tungstates, thiosulfates, cerates and the like. The halides may also be present, including fluoride, chloride, bromide and iodide.

It is well recognized that many anions have complex chemistries and may exist in one or more forms, for example, orthovanadate and metavanadate; and the various molybdate oxyanions such as $MoO_4^{-2}$, and $Mo_7O_{24}^{-6}$ and $Mo_2O_7^{-2}$. The oxyanions may also include mixed metal-containing oxyanions including polyoxyanion structures. For instance, manganese and molybdenum can form a mixed metal oxyanion. Similarly, other metals, whether provided in anionic, cationic, elemental or covalent form may enter into anionic structures.

While an oxyanion, or a precursor to an oxyanion, may be used in solutions impregnating a carrier, it is possible that during the conditions of preparation of the catalyst and/or during use, the particular oxyanion or precursor initially present may be converted to another form. Indeed, the element may be converted to a cationic or covalent form. In many instances, analytical techniques may not be sufficient to precisely identify the species present. The invention is not intended to be limited by the exact species that may ultimately exist on the catalyst during use.

With certain highly efficient catalysts, the most preferred promoter comprises rhenium, which can be provided in various forms, for example, as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $ReO_4$. Similar chemistries can be exhibited by other metals such as molybdenum and tungsten.

Another class of promoters, which may be employed with the present invention, includes manganese components. In many instances, manganese components can enhance the activity, efficiency and/or stability of catalysts. The manganese species that provides the enhanced activity, efficiency and/or stability is not certain and may be the component added or that generated either during catalyst preparation or during use as a catalyst. Manganese components include, but are not limited to, manganese acetate, manganese ammonium sulfate, manganese citrate, manganese dithionate, manganese oxalate, manganous nitrate, manganous sulfate, and manganate anion, for example permanganate anion, and the like. To stabilize the manganese component in certain impregnating solutions, it may be necessary to add a chelating compound such as ethylenediaminetetraacetic acid (EDTA) or a suitable salt thereof.

The amount of anion promoter may vary widely, for example, from about 0.0005 to 2 wt. %, preferably from about 0.001 to 0.5 wt. % based on the total weight of the catalyst. When used, the rhenium component is often provided in an amount of at least about 1, say, at least about 5, for example, about 10 to 2000, often between 20 and 1000, ppmw calculated as the weight of rhenium based on the total weight of the catalyst.

It is desirable that the silver and one or more solid promoters be relatively uniformly dispersed on the carrier. A preferred procedure for depositing silver catalytic material and one or more promoters comprises: (1) impregnating a carrier according to the present invention with a solution comprising a solvent or solubilizing agent, silver complex and one or more promoters, and (2) thereafter treating the impregnated carrier to convert the silver compound and effect deposition of silver and the promoter (s) onto the exterior and interior pore surfaces of the carrier. Silver and promoter depositions are generally accomplished by heating the solution containing carrier at elevated temperatures to evaporate the liquid within the carrier and effect deposition of the silver and promoters onto the interior and exterior carrier surfaces. The temperature of the heating step is high enough to reduce any silver compounds to metallic silver. Impregnation of the carrier is the preferred technique for silver deposition because it utilizes silver more efficiently than coating procedures, the latter being generally unable to effect substantial silver deposition onto the interior surfaces of the carrier. In addition, coated catalysts are more susceptible to silver loss by mechanical abrasion.

Well known methods can be employed to analyze for the amounts of silver and solid promoters deposited onto the alumina carrier. The skilled artisan may employ, for example, material balances to determine the amounts of any of these deposited components. Alternatively, any suitable analytical technique for determining elemental composition, such as X-ray fluorescence (XRF), may be employed to determine the amounts of the deposited components.

As is known in the art, as a reaction is carried out over a catalyst over a period of time, the catalyst eventually begins to "age" and lose activity, which typically means that the number of active sites available for catalyzing the desired reaction are reduced. One mechanism by which such aging occurs involves the formation of silver chloride on the catalyst surface. Silver chloride is thought to form irreversibly, causing a reduction in catalyst life and more frequent catalyst replacement. The presence of silver chloride on a discharged catalyst may be determined using any suitable analytical technique, such as x-ray diffraction (XRD), alone or in combination with element-specific measurements for quantification of Cl species, such as x-ray fluorescence (XRF) or leaching of the discharged catalyst followed by analysis of the leachate by ion chromatography, titration, or the like.

Sulfur is a poison for many catalysts, including high-efficiency alkylene oxide catalysts. In typical alkylene oxide processes, sulfur is an impurity that enters the process as various sulfur-containing compounds contained in the alkylene feed, and/or the ballast gas. In certain alkylene oxide processes, the concentration of sulfur in the reactor feed on an atomic basis may vary from as little as a couple parts per billion (molar) based on the amount of ethylene to nearly 50 ppb (molar) over the life of the process. At any given time, the concentration of sulfur in the reactor feed gas may be much higher. The sulfur may be present in a variety of different sulfur-containing compounds, including without limitation sulfides (including hydrogen sulfide and disulfides), mercaptans (e.g., methyl mercaptan), sulfur oxides (e.g., $SO_2$), thiophenes, and carbonyl sulfide (COS). Accordingly, in one exemplary embodiment, the concentration of sulfur in the reactor feed 22 is controlled in order to control the formation of silver chloride on the high-efficiency alkylene oxide catalyst in reactor 10. Any method for controlling the sulfur concentration—including both manual and automated methods—may be used. The concentration of sulfur in reactor feed 22 on an atomic basis is preferably controlled to no more than about 50 ppbv. Concentrations of no more than about 40 ppbv are preferred, and concentrations of no more than about 30 ppbv are even more preferred. Concentrations of no more than about 20 ppbv are still more preferred, and concentrations of not more than about 5 ppbv are further preferred. In certain especially preferred examples, the reactor feed gas sulfur concentration on an atomic basis is no more than about 1 ppbv.

When a fresh (unused) catalyst is first started up, it does not immediately achieve its ultimate level of performance. Generally, immediately upon startup both activity and efficiency are somewhat lower than the catalyst will eventually obtain. As the fresh catalyst is operated, the activity and efficiency increase over a period of a few days, until they asymptotically approach a steady state operating condition, at which time the change in the catalyst activity is less than the standard deviation of the measurements. This increase in performance for the first few days of operation is generally referred to as "activation" of the catalyst, and the catalyst is said to be fully "activated" once this period of operation is complete. An "activation period" is a period of time during which catalyst activation takes place. The term "activation period" includes but is not limited to the period of time during which activation reaches completion. The exact mechanism of activation has not been well established, but may be due to some rearrangement or redistribution of the solid-phase promoters on the catalyst surface.

The effect of sulfur concentration in the alkylene feed on silver chloride formation is believed to be more pronounced for catalysts that have not been completely activated. In certain exemplary processes, the alkylene oxide process is operated for an activation period of at least about two days, and more preferably at least about six days, in order to reduce the likelihood or extent of silver chloride formation on the catalyst. In other exemplary processes, the sulfur concentration in the reactor feed during activation is allowed to vary, even to levels higher than 50 ppbv. In further exemplary processes, the concentration of sulfur in the reactor feed (on an atomic basis) during activation is controlled to not more than about 50 ppbv, more preferably not more than about 30 ppbv, and even more preferably not more than about 20 ppbv, with concentrations of not more than about 5 ppbv and 1 ppbv being further preferred and most preferred, respectively. In other exemplary processes, the concentration of sulfur on the reactor feed gas is maintained at the foregoing levels for a period of time that is preferably at least about two days, more preferably at least about four days, and even more preferably at least about seven days.

Referring again to FIG. 1, alkylene feed 12 may be provided by alkylene source 70 such as an olefin unit that is integrated and/or on-site with alkylene oxide process 20. Alkylene source 70 may also be operated by a third party or at a location remote from alkylene oxide process 20. In one embodiment, a desulfurizing unit 72 is provided to remove sulfur-containing compounds from the alkylene(s) received from alkylene source 70. Desulfurizing unit 72 receives untreated alkylene feed gas stream 11a and desulfurizes it to yield desulfurized alkylene feed gas stream 12. Valve 74 allows desulfurizing unit 72 to be selectively fluidly coupled to alkylene source 70. Valve 74 may be operated manually or automatically. In addition, a bypass line may be provided around desulfurizing unit 72 so that the untreated alkylene feed gas stream 11a may be selectively and directly fluidly coupled to process 20. As used herein, the term "desulfurized" refers to a composition that has been subjected to a sulfur removal process (e.g., a desulfurizing unit) and is not limited to those compositions having zero sulfur content. As shown in FIG. 1, the desulfurized alkylene feed gas 12 from desulfurizing unit 72 is fluidly coupled to reactor feed gas inlet 22. Intervening units or processes may be included between desulfurizing unit 72 and alkylene oxide reactor 10. However, in the example of FIG. 1, desulfurized alkylene feed gas outlet 12 from desulfurizing unit 72 is directly fluidly coupled to desulfurized reactor feed gas inlet 22 such that no intervening processes are provided between them. As discussed previously, desulfurized alkylene feed gas 12 is combined with an organic chloride gaseous promoter stream 14 and oxygen (or air) stream 15 plus, optionally, ballast gas 13 before entering reactor 10. Alkylene feed flow controller 51 regulates the flow rate of the desulfurized alkylene feed 12 to reactor 10 as measured by flow meter 41. Organic chloride gaseous promoter flow controller 36 regulates the flow of the organic chloride gaseous promoter as measured by flow meter 44.

Desulfurizing unit 72 may comprise any known process for removing sulfur-containing compounds to the desired levels. In one preferred embodiment, desulfurizing unit 72 comprises an adsorbent bed through which untreated alkylene feed from stream 11a passes, causing at least a portion of the sulfur-containing compounds to be adsorbed to the bed and removed from desulfurized alkylene feed 12. Numerous adsorbents for sulfur-containing compounds are known and may be used in an adsorbent bed comprising desulfurizing unit 72. The adsorbent material comprising the adsorbent bed is preferably selected to adsorb one or more of the sulfur-containing compounds described above. The adsorbent may adsorb the sulfur-containing compounds by physical and/or chemical adsorption processes. In certain exemplary implementations, the adsorbent comprises a granular inorganic material. In certain examples, the inorganic material is an inorganic oxide, which is preferably a metal oxide and more preferably a rare earth metal oxide, a transition metal oxide, and/or mixtures thereof. Suitable metal oxides include without limitation, oxides of zinc, copper, iron, manganese, lead, aluminum, vanadium, calcium, barium, cerium, lanthanum, and mixtures thereof. Zinc oxide is particularly suited for adsorbing hydrogen sulfide. Alumina-based adsorbents are particularly suited for adsorbing mercaptans, sulfides, disulfides, and thiophenes. In the case of zinc oxide adsorbents, hydrogen sulfide reacts with the zinc oxide to yield solid zinc sulfide and water:

$$H_2S+ZnO \rightarrow ZnS+H_2O \qquad (3)$$

The removal of hydrogen sulfide proceeds as a chemical reaction. Thus, the adsorbent bed dimensions may be determined using known reaction engineering principles. In certain examples, the zinc oxide bed is operated at an elevated temperature (relative to ambient). In other examples, the bed temperature is at least about 200° C., preferably at least 210° C., more preferably at least about 220° C., even more preferably about 230° C., and still more preferably at least about 240° C. In some cases, the bed temperature is operated at temperatures of up to about 250° C. or higher.

If sulfur-containing compounds other than hydrogen-sulfide are present in untreated alkylene feed 11, adsorbent beds other than zinc oxide are preferably used, such as the alumina-based adsorbents mentioned above. Suitable alumina-based adsorbents include Selexsorb® SG, Selexsorb® COS, Selexsorb® CDX, and UOP SG-731. The particular type and configuration of adsorbents are selected based on the species of sulfur to be removed, as well as their concentrations in the alkylene feed supplied by source 70. Selexsorb® SG is a smooth alumina-based spherical promoter-impregnated adsorbent that is supplied by BASF Corporation and which adsorbs sulfur-containing compounds including sulfides, disulfides, and thiophenes. It has a surface area of about 200 $m^2/g$, a packed bulk density of about 832 $kg/m^3$, and contains about 95 percent by weight alumina and promoter. Selexsorb® COS is a smooth, spherical, alumina-based adsorbent that selectively adsorbs COS, $CO_2$, $H_2S$, and $CS_2$. Selexsorb® CDX is also a smooth, spherical, alumina-based adsorbent that selectively adsorbs sulfur-based compounds including mercaptans, disulfides, and thiophenes. In addition to alumina-based adsorbents, in certain examples a copper/zinc adsorbent may be used to provide desulfurization. One known copper/zinc adsorbent is Actisorb 301, which is supplied by Sud-Chemie. As discussed below, in certain examples a combination zinc oxide/copper oxide bed is used in desulfurizing unit 72. In one such example, the combination zinc oxide/copper oxide bed operates at a temperature that is preferably at least about 50° C., more preferably at least about 60° C., and even more preferably at least about 70° C. The zinc oxide/copper oxide bed temperature is preferably no more than about 120° C., more preferably no more than about 110° C., and even more preferably no more than about 100° C.

Figure 2A:
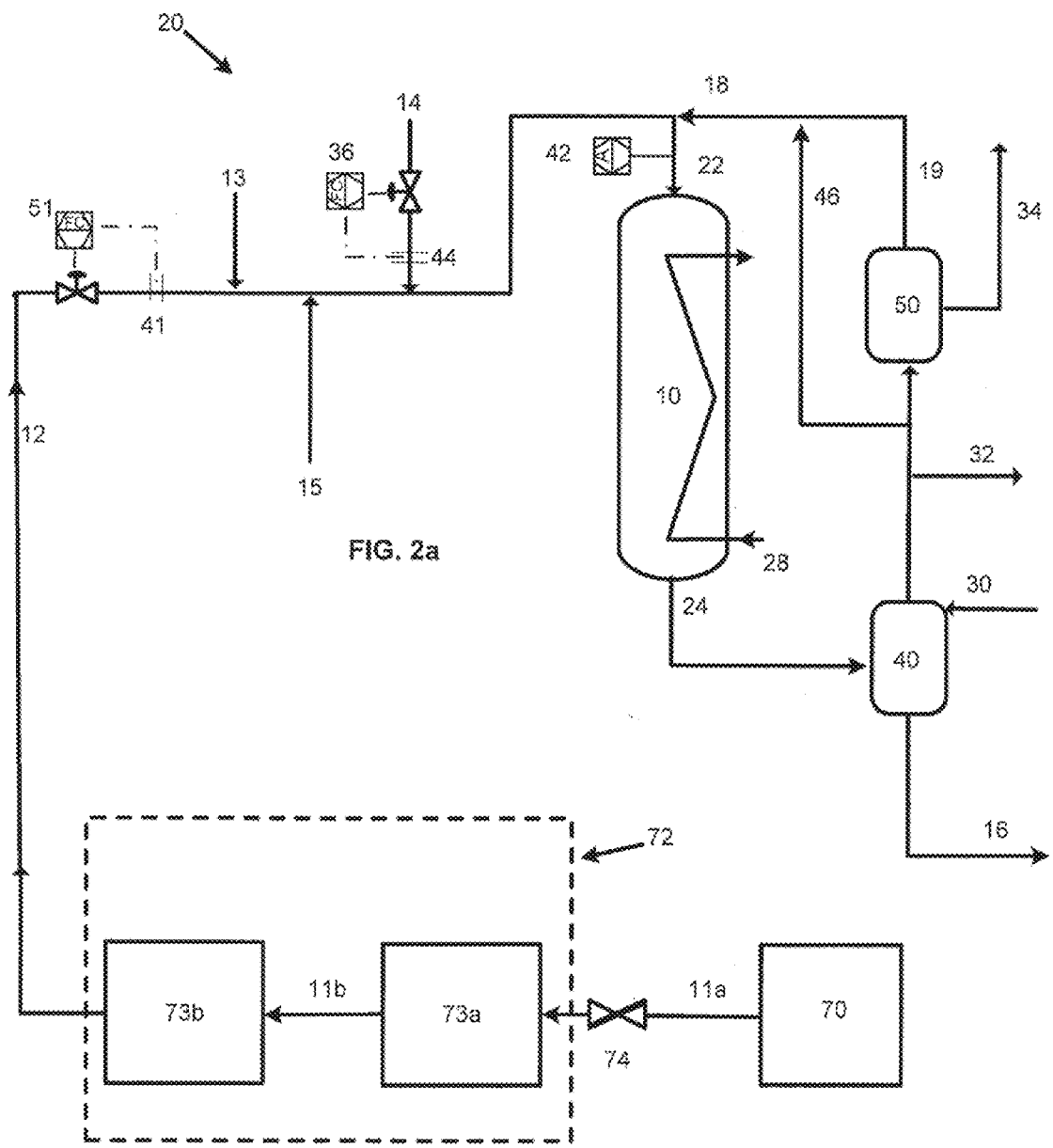
FIG. 2a is a process flow diagram depicting an embodiment of a process for making an alkylene oxide by epoxidizing an olefin which includes a sulfur conversion unit and a hydrogen sulfide adsorbent bed.

In certain implementations, sulfur-containing compounds other than $H_2S$ may be converted to $H_2S$ and then removed on an $H_2S$ adsorbing bed, such as zinc oxide. Referring to FIG. 2a, desulfurizing unit 72 comprises a sulfur conversion unit 73a and a hydrogen sulfide adsorber 73b. Alkylene feed source 70 supplies untreated alkylene feed stream 11a which is fluidly coupled to sulfur conversion unit 73a. Sulfur conversion unit 73a converts non-$H_2S$ sulfur-containing compounds (e.g., mercaptans, sulfates, and COS) to $H_2S$ and produces a product stream 11b that is fluidly coupled to the inlet of hydrogen sulfide adsorber 73b. In one example, sulfur conversion unit 73a may comprise a hydrogenation catalyst and a source of hydrogen for converting non-$H_2S$ sulfur-containing compounds to $H_2S$. However, this process may result in partial olefin loss if the olefin is itself hydrogenated. In another example, sulfur conversion unit 73a comprises a hydrolysis catalyst for hydrolyzing COS to produce H2S according to the following reaction:

$$COS+H_2O \rightarrow CO_2+H_2S \quad (4)$$

Examples of metal oxides suitable for carrying out the hydrolysis of COS include without limitation oxides of one or more metals selected from the group consisting of alkali earth metals such as Li, Na, K, Cs or the like, alkaline earth metals such as Mg, Ca, Ba, or the like, Group IIb metals such as Zn, Cd or the like, and Group IV metals such as Sn, Pb, or the like. Such metal oxide hydrolysis catalysts are described in Nozue, et al., U.S. Pat. No. 4,511,668, the contents of which are hereby incorporated by reference in their entirety. In another example, alumina is hydrated in the presence of the non-$H_2S$ sulfur containing compounds to convert the compounds to $H_2S$.

Figure 2B:
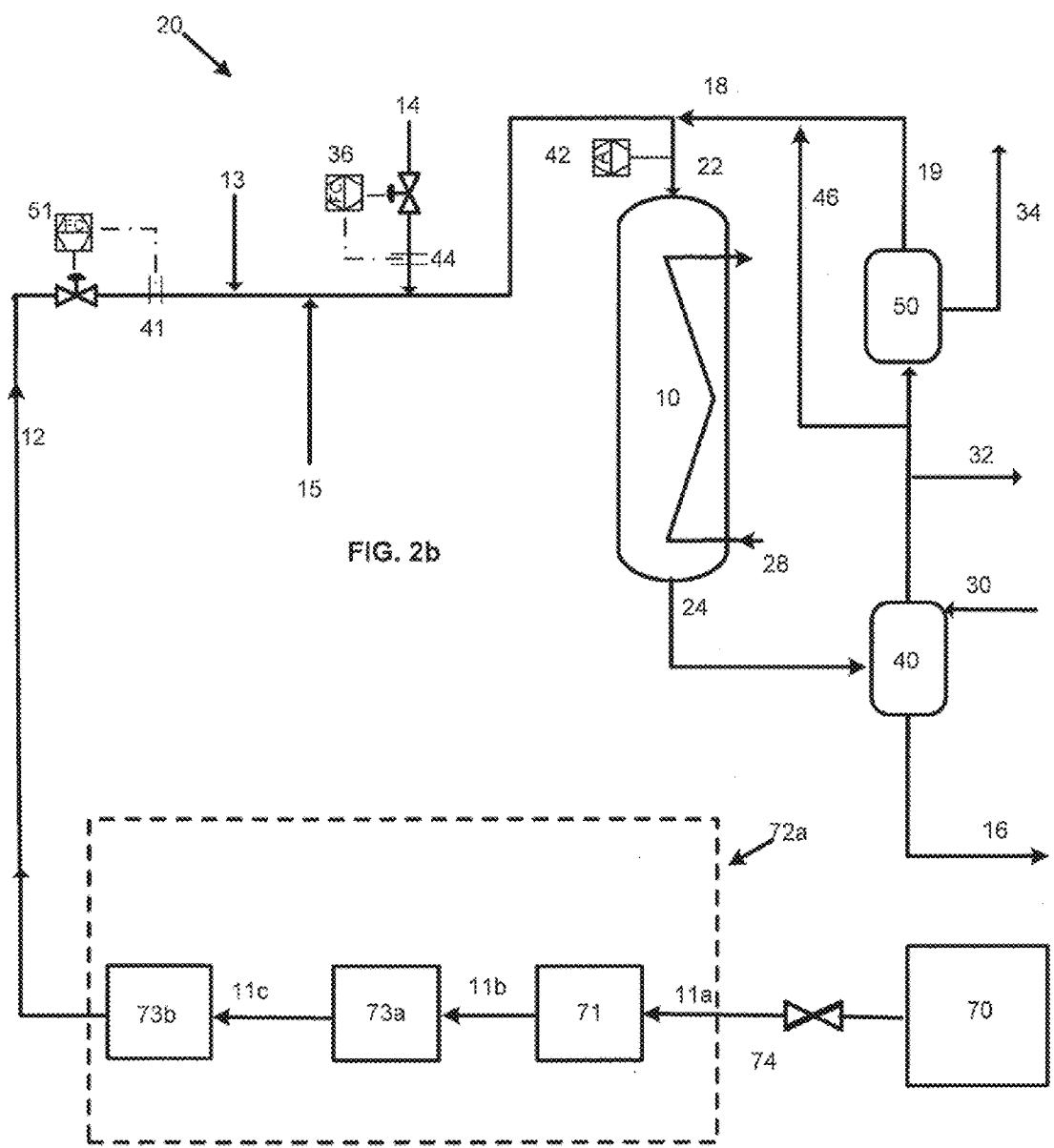
FIG. 2b is a process flow diagram depicting an embodiment of a process for making an alkylene oxide by epoxidizing an olefin which includes a heavy hydrocarbon contaminant pretreater, a sulfur conversion unit, and a hydrogen sulfide adsorbent bed.

In certain exemplary processes, untreated alkylene feed source 70 may supply alkylenes with oil or other heavy hydrocarbon contaminants. It may be desirable to remove such contaminants prior to desulfurization to preserve the integrity and operation of the sulfur-compound adsorbing bed(s) in desulfurization unit 72. Referring to FIG. 2b, feed pretreater 72a comprises a heavy hydrocarbon contaminant pretreater 71 upstream of sulfur conversion unit 73a and desulfurization unit 73b. In an alternate implementation, sulfur conversion unit 73a is eliminated, and desulfurization unit 73b is configured to remove the desired sulfur-containing species in product stream 11b from heavy hydrocarbon contaminant pretreater 71. Processes for removing such heavy hydrocarbon contaminants are known to those skilled in the art and include activated carbon bed processes, filters, and low temperature traps that condense and remove the contaminants. The use of an activated carbon bed as a heavy hydrocarbon contaminant pretreater is particularly beneficial because it generally provides some additional sulfur-containing compound adsorption.

In addition to adsorbent beds of the type described previously, desulfurizing unit 72 may also comprise an acid gas removal process, such as a liquid-vapor contactor (e.g., a scrubber). The scrubber includes a liquid scrubbing agent that removes hydrogen sulfide into the liquid phase and produces desulfurized alkylene feed gas 12. Preferred scrubbing agents are basic compounds, including without limitation amine compounds and sodium hydroxide (caustic). Examples of suitable amine compounds include hydroxy amines, including primary, secondary, and tertiary hydroxy amines. Specific examples of suitable amine scrubbing compounds include monoethanolamine (MEA) and diethanolamine (DEA). The scrubber may be a semi-batch system in which the scrubbing agent remains in a scrubber vessel or may be a fully continuous flow system in which the scrubbing agent and the alkylene feed gas both flow through the vessel. The flow rates, and scrubbing agent concentrations (and/or scrubbing agent volume in the case of a semi-batch system) are preferably selected to provide the desired degree of sulfur-containing compound removal. The temperature of the scrubber may also be adjusted to control the extent of desulfurization. If alkylene feed source 70 comprises an existing olefin unit with its own acid gas removal process, the process may be adjusted in order to provide the necessary desulfurization. However, typical specifications for olefin feed do not call for the degree of desulfurization required to prevent silver chloride formation on a high-efficiency silver catalyst. It should also be noted that various combinations of the foregoing desulfurization processes may be used. Thus, in one example, an acid gas scrubber, an $H_2S$ conversion unit, and one or more desulfurizing units (e.g., various combinations of activated carbon or metal oxide adsorbent beds of the type described previously) suitable for removing $H_2S$ and/or other sulfur-containing species are used. In addition, one or more desulfurizing units may be provided and selected to have different affinities for different sulfur-containing compounds. Thus, for example, one desulfurizing unit may generally adsorb all sulfur-containing species, while another may selectively adsorb specific sulfur-containing species. In another example, the foregoing processes are combined with a heavy hydrocarbon contaminant pretreater.

In certain examples, desulfurizing unit 72 operates at a pressure of at least about 220 psig, more preferably at least about 260 psig, and even more preferably at least about 280 psig. In other examples, desulfurizing unit 72 operates at a pressure of not more than about 340 psig, more preferably not more than about 320 psig, and even more preferably not more than about 310 psig. The adsorbent bed or beds comprising desulfurizing unit 72 are preferably sized to provide a contact time with the incoming gas that is sufficient to provide the desired degree of desulfurization. In one example, each bed is sized to provide a superficial velocity, i.e., flow rate/area of the vessel normal to flow without adsorbent, of not more than about 20 cm/sec, preferably not more than about 10 cm/sec, and more preferably not more than about 5 cm/sec.

Figure 2C:
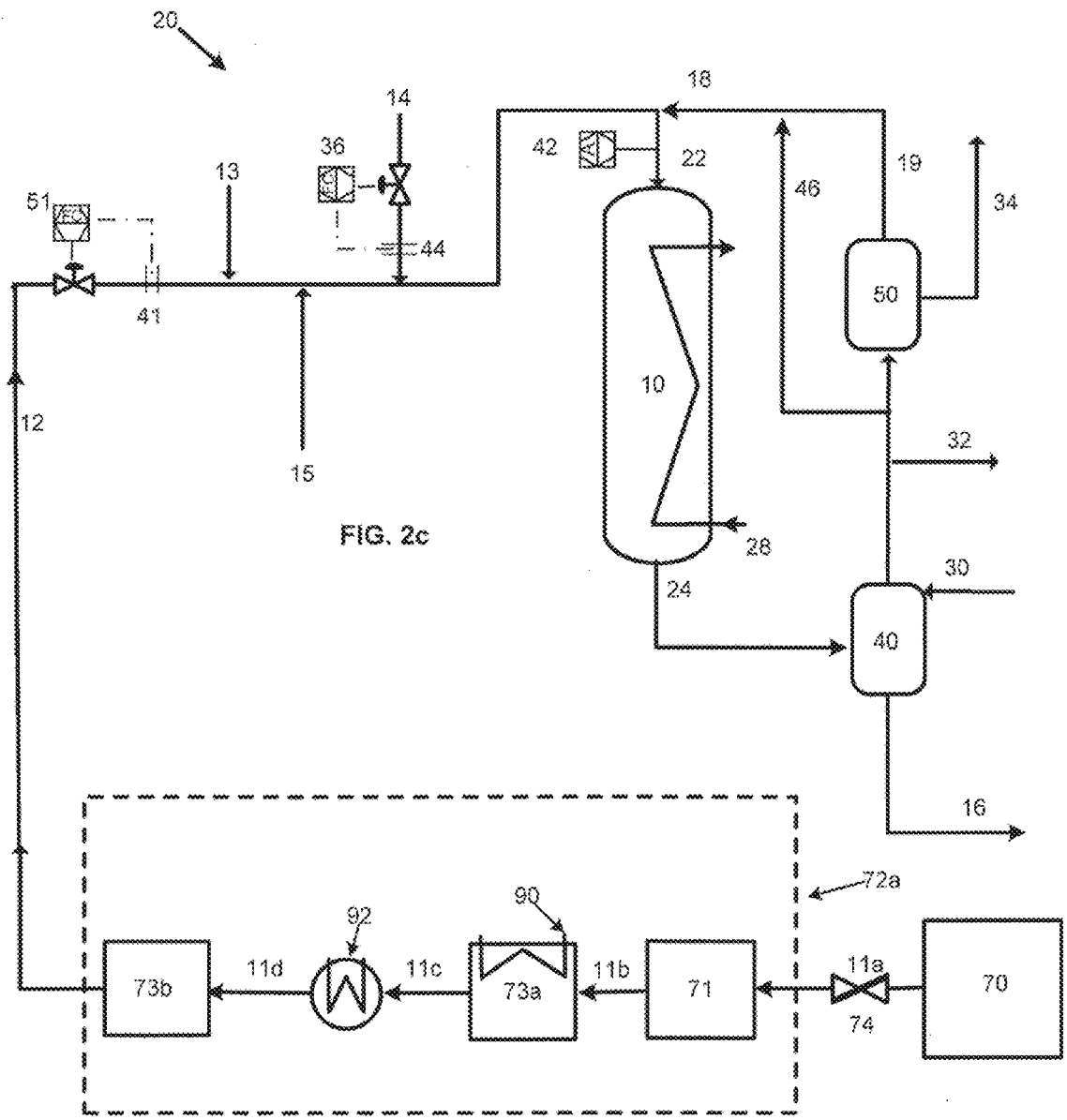
FIG. 2c is a process flow diagram depicting an embodiment of a process for making an alkylene oxide by epoxidizing an olefin which includes a heavy hydrocarbon contaminant pretreater and multiple desulfurizing units.

Another exemplary process for controlling the reactor feed gas sulfur concentration is depicted in FIG. 2c. In the process of FIG. 2c, feed pretreater 72a includes a heavy hydrocarbon contaminant pretreater 71, a first desulfurizing unit 73a, and a second desulfurizing unit 73b. Heavy hydrocarbon contaminant pretreater 71 is configured to remove oils or other heavy hydrocarbon contaminants, and optionally, some sulfur containing species from the alkylene feed. It may include activated carbon bed processes, filters, and low temperature traps that condense and remove the contaminants or combinations of such components. However, in the example of FIG. 2c, heavy hydrocarbon contaminant pretreater 71 comprises activated carbon granules.

First desulfurizing unit 73a receives heavy hydrocarbon contaminant pretreater products stream 11b and is configured to remove small amounts of hydrogen sulfide and all other sulfur species, including mercaptans and thiophenes. In a preferred implementation, first desulfurizing unit 73a uses a chemisorption process. One suitable chemical adsorption medium is Actisorb 301, a copper/zinc adsorbent catalyst supplied by Sud-Chemie. In certain examples, it is preferable to adjust the operating temperature of first desulfurizing unit 73a to a temperature favoring adsorption. In particular, it has been found that the temperature of first desulfurizing unit 73a can be adjusted to improve chemical adsorption by a copper/zinc catalyst. Thus, a heat source 90 (e.g., a heating coil with a controllable heating medium, such as steam) may be used to selectively regulate the temperature of first desulfurizing unit 73a. In one example wherein first desulfurizing unit 73a includes a copper/zinc Actisorb 301 adsorbent, the temperature of first desulfurizing unit 73a is preferably at least about 50° C., more preferably at least about 60° C., and even more preferably at least about 70° C. In accordance with the example, the temperature of the first desulfurizing unit 73a is preferably no more than about 120° C., more preferably no more than about 110° C., and even more preferably no more than about 100° C. The pressure of first desulfurizing unit 73a is generally at least about 220 psig, preferably at least about 260 psig, and even more preferably at least about 280 psig. The pressure of first desulfurizing unit 73a is generally not more than about 340 psig, preferably not more than about 320 psig, and even more preferably not more than about 310 psig. The adsorbent bed of second desulfurizing unit 73b receives product stream 11d from first desulfurizing unit 73a and is preferably sized to provide a contact time with the incoming gas that is sufficient to provide the desired degree of desulfurization. In one example, the bed is sized to provide a superficial velocity of not more than about 20 cm/sec, preferably not more than about 10 cm/sec, and more preferably not more than about 5 cm/sec. If desired, a sulfur conversion unit may be added to feed pretreater 72a or used in lieu of one of the desulfurizing units 73a and 73b.

Whereas first desulfurizing unit 73a is configured to remove hydrogen sulfide and all other sulfur-containing species, second desulfurizing unit 73b is configured to selectively remove particular sulfur-species. In one example, second desulfurizing unit 73b is configured to selectively adsorb COS, hydrogen sulfide, and $CS_2$. One suitable adsorbent that can be used in second desulfurizing unit 73b is Selexsorb® SG. If first desulfurizing unit 73a includes heat source 90, such as to improve chemisorption, and second desulfurizing unit 73b uses a physical adsorption medium, interstage cooler 92 is preferably provided to reduce the temperature of feed stream 11d to second desulfurizing unit 73b to a temperature that favors physical adsorption.

In certain preferred embodiments, desulfurizing unit 72 or feed pretreater 72a are operated to maintain the concentration of sulfur in reactor feed gas 22 below a predetermined value. In accordance with such embodiments, analyzer 42 is preferably configured to detect sulfur concentrations in the parts per billion (volume) range in reactor feed gas 22. Based on the detected sulfur concentrations, operating parameters (e.g., temperature of desulfurizing unit 73a) are adjusted to maintain the concentration of sulfur in reactor feed gas 22 below the desired value. The adjustments to desulfurizing unit 73a may be made in an open or closed loop fashion. However, in one embodiment, desulfurizing unit 73a is provided with a heat source 90 and a temperature controller, the set point of which can be adjusted to maintain the desired sulfur concentration in reactor feed gas 22. In addition, if alkylene feed source 70 provides an unacceptably high concentration of sulfur, valve 74 may be closed to isolate alkylene feed source 70 from process 20. In that case, another alkylene feed source is preferably placed in fluid communication with process 20, as will be discussed below. If closed loop control is provided, a composition controller may be provided which controls the concentration of sulfur detected by analyzer 42. The composition controller may be cascaded to reset the setpoint of the appropriate controller (e.g., temperature controller in the desulfurization unit 73a or any other desulfurizing unit in which an adjustable heat or cooling source is provided).

If analyzer 42 is used to measure the concentration of sulfur in reactor feed gas 22, it is preferably located on-line or in-line to minimize travel of the sample from the process line to the analyzer 42. The use of such analyzers eliminates the need for sample containers, such as gas bombs, that may have a tendency to adsorb sulfur-containing compounds, thereby reducing the accuracy of measurement of such compounds in the process gas. Analyzer 42 is preferably a gas chromatograph (GC) and is also preferably constructed of materials that are inert or nearly inert towards the adsorption of sulfur-containing compounds. Suitable materials include silica-lined tubing, electropolished tubing, and TEFLON®. Any suitable chromatography column or combination of columns may be used in the GC to separate the sulfur-containing compounds from the other compounds. Certain porous-layer open tubular (PLOT) columns, such as the Agilent part number 19095-UO4, have been found to be especially suitable for this purpose. Other types of analyzers such as so-called paper-tape analyzers may also be used. However, skilled artisans will be aware of other suitable columns.

In order to provide the desired sulfur-detection sensitivity, analyzer 42 also preferably includes a flame photometric detector (FPD) to enhance the sensitivity of the measurement. Other sulfur-sensitivity enhancing components may included in analyzer 42 such as sulfur chemiluminescent systems, cryofocusing systems, or targeted signal enhancement systems. See R. Aaron Eidt, "Targeted Signal Enhancement (TSE), A Powerful Means of Boosting Process GC Detection Limits by 1-2 Orders of Magnitude," Presented at IFPAC® 2007 (Baltimore, Md.).

Figure 3:
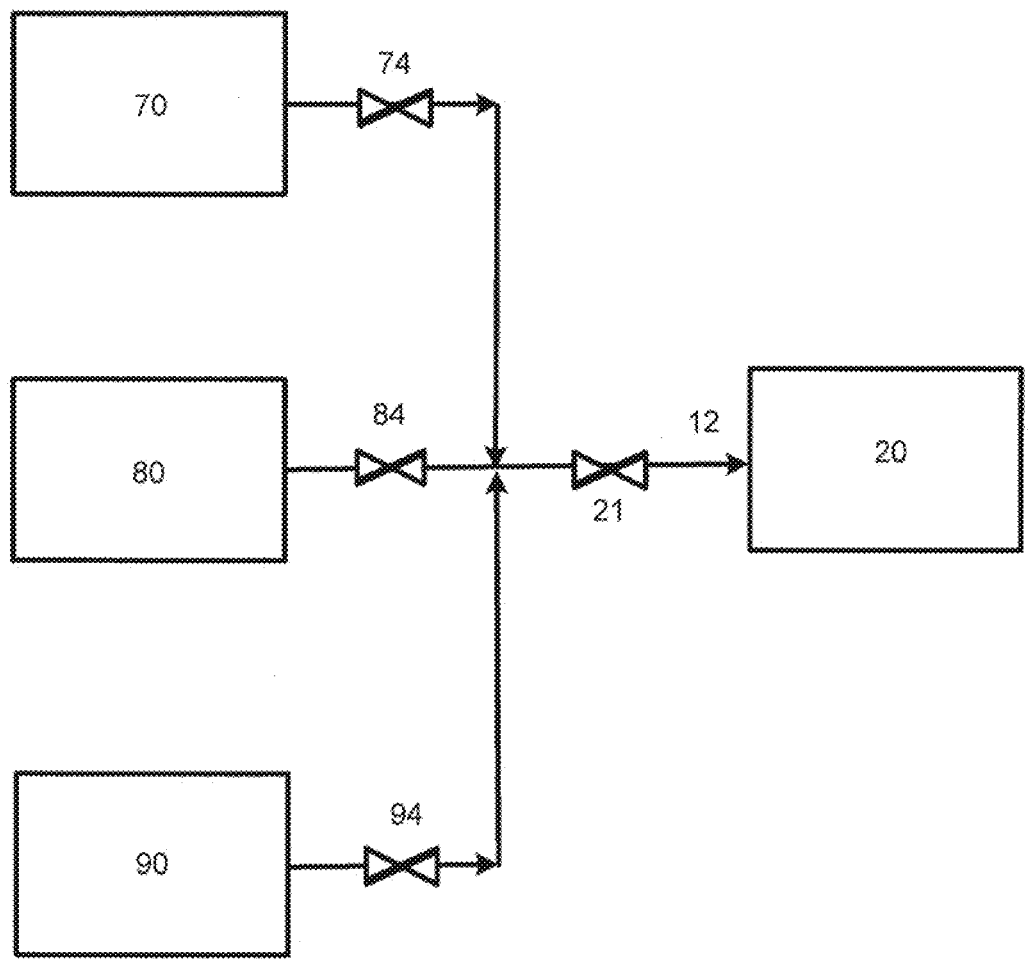
FIG. 3 is a process flow diagram depicting an alkylene oxide manufacturing process in which a plurality of alkylene feed gas sources are configured for selective fluid coupling to the alkylene oxide unit of FIG. 1.

In certain exemplary implementations, one or more alkylene oxide feed sources are selectively fluidly coupled to process 20 to control the concentration of sulfur-containing compounds in reactor feed gas 22. One illustration is provided in FIG. 3. Three alkylene oxide feed sources 70, 80, and 90 are each independently coupled to process 20 so that any or all of them may supply alkylene oxide to process 20 at any given time. Feed sources 70, 80, and 90 may be provided within the same facility as process 20, or one or more of them may be provided remotely to process 20. In addition, one or more of the feed sources 70, 80, and 90 may be a mobile feed source that is selectively connected to process 20. In addition, one or more of the feed sources 70, 80, and 90 may be located remotely from the facility in which process 20 is located.

Each feed source 70, 80, 90 has its own respective fluid coupling valve 74, 84, 94 which may be a manually operated or automatically operated to selectively and independently fluidly couple the corresponding feed source 70, 80, and/or 90 to process 20. In certain illustrative examples, one or more of the feed sources 70, 80, and/or 90 is selectively coupled to process 20 to control the sulfur concentration of alkylene feed gas stream 12. In another example, one or more of the feed sources 70, 80, and/or 90 is selectively coupled to process 20 to control the concentration of sulfur in reactor feed gas stream 22, for example, as indicated by analyzer 42. In addition, one or more of the alkylene oxide feed sources may undergo desulfurization prior to entering process 20. The combined feed sources may also undergo desulfurization at process 20, as discussed above with respect to FIGS. 1 and 2. Valve 21 may be used to simultaneously isolate feed sources 70, 80, and 90 from process 20.

In one exemplary implementation, valves 74, 84, and 94 are opened only when their corresponding feed sources produce an alkylene oxide stream 12 with a sulfur concentration that is no more than about 50 ppbv, preferably no more than about 40 ppbv, more preferably no more than about 30 ppbv, still more preferably no more than about 20 ppbv, yet more preferably not more than about 10 ppv, even more preferably no more than about 5 ppv, and in an especially preferred example, no more than about 1 ppv of the reactor feed gas 22. As will be apparent to those skilled in the art, the actual sulfur concentration in the alkylene oxide stream 12 provided by feed sources 70, 80, and/or 90 may differ from that of reactor feed gas stream 22 because the flow rates of ballast gas 13 and oxygen 15 will affect the sulfur concentration in reactor feed gas 22.

Example 1

80 cc of a silver-based, high efficiency, rhenium-promoted ethylene oxide catalyst is charged to an autoclave reactor. Upstream of the reactor, an ethylene feed is desulfurized by contacting a first bed of Actisorb 301 followed by a second bed of Selexsorb® SG at ambient temperature and a pressure of about 295 psig (2030 kPa-gauge). The flow rate of ethylene to the beds varies from about 500-550 scfh (14.1-15.6 standard $m^3$ per hour). Each bed is made of a four inch (10-cm) ID pipe with a length of about 48 inches (1.2 m). The first bed contains 23.0 lbs (10.4 kg) of Actisorb 301, and the second bed contains 17.0 lbs. (7.71 kg) of Selexsorb SG. This same desulfurization system is employed for the runs of Examples 2-5.

Based on the amount of sulfates found on the discharged catalysts of Examples 1-5, as shown in Table 1 below, and the estimated percentage of feed gas sulfur that is adsorbed on the catalyst, it is estimated that the amount of sulfur in the feed gas on an atomic basis is about 15 ppbv following desulfurization of the ethylene in the first and second beds.

The reactor is started up at standard conditions (8 mole-% oxygen, 30 mole-% ethylene, 3 mole-% carbon dioxide, 0.5 mole-% ethane, 2 ppmv ethyl chloride, balance nitrogen, temperature 240° C., pressure 275 psig (1900 kPa-gauge) and at gas hourly space velocity of 6,600 $hr^{-1}$) and the catalyst is allowed to activate for about six days. At the end of the activation period, the reactor conditions are changed to conditions favorable to the formation of AgCl (10 mole-% oxygen, 30 mole-% ethylene, 7 mole-% carbon dioxide, 0.4 mole-% ethane, 14 ppmv ethyl chloride, balance nitrogen, temperature 270° C., pressure 275 psig (1900 kPa-gauge) and at gas hourly space velocity of 8,200 $hr^{-1}$). The ethyl chloride concentration is higher than that used in typical commercial processes in order to reduce the length of the experiment. However, the conditions are believed to provide results that are representative of those obtained with typical commercial reactor run times and organic chloride concentrations. About one day later, a gas mixture composed of 0.025 mole-% hydrogen sulfide, 50 mole-% methane and balance nitrogen acquired from Airgas is added to the reactor feed, corresponding to about 0.025 ppmv (25 ppbv) of hydrogen sulfide based on the reactor feed flow rate (making the total feed sulfur concentration on an atomic basis about 40 ppbv). The reactor is operated at these conditions for about 20 days. The catalyst is removed from the reactor and analyzed. The discharged catalyst is found to contain about 1.75 wt % of AgCl.

Example 2

80 cc of the same batch of ethylene oxide catalyst from Example 1 is charged to an autoclave reactor and started up in the same manner as in Example 1. After about six days, operating conditions are changed to the same conditions favorable for AgCl formation as in Example 1. However, in this case no hydrogen sulfide is added to the reactor feed. The reactor is operated for about another 19 days and shut down. The catalyst is removed and analyzed. AgCl is not detected on the catalyst when analyzed by X-ray fluorescence and X-ray diffraction.

Example 3

80 cc of the same batch of ethylene oxide catalyst as used in Example 1 is charged to an autoclave reactor. The reactor is started up at the conditions favorable for AgCl formation given in Example 1. At about the same time, a small feed of hydrogen sulfide is started to the reactor, corresponding to about 0.025 ppmv (25 ppbv) of hydrogen sulfide based on the reactor feed flow rate. The reactor is operated at these conditions for about 22 days and shut down. The catalyst is removed from the reactor and analyzed. The discharged catalyst contains about 2.7 wt % AgCl. This example shows that catalyst activation time has a significant effect on silver chloride formation when certain concentrations of sulfur-containing compounds are present in the alkylene oxide reactor feed.

Example 4

80 cc of the same batch of ethylene oxide catalyst as used in Example 1 is charged to an autoclave reactor. The reactor is started up at the conditions favorable for AgCl formation given in Example 1, without hydrogen sulfide addition to the feed, and the catalyst is then allowed to activate for about four days. At the end of the activation period, the reactor temperature is changed to 255° C. At about the same time, a small feed of hydrogen sulfide is started to the reactor, corresponding to about 0.025 ppmv (22 ppbv) of hydrogen sulfide based on the reactor feed flow rate. The reactor is operated at these conditions for about two days and the reactor temperature is then increased to 270° C. The reactor is maintained at these conditions for about another 20 days and shut down. The catalyst is removed from the reactor and analyzed. The discharged catalyst contains about 2.6 wt % of AgCl. In comparison to Example 1, this example again shows that catalyst activation time has a significant effect on silver chloride formation when certain concentrations of sulfur-containing compounds are present in the alkylene oxide reactor feed. Furthermore, comparing the AgCl levels for Examples 3 and 4 demonstrates that the specific conditions during the activation period without deliberate addition of sulfur-containing compounds to the feed do not significantly affect the ultimate AgCl level Example 5

80 cc of the same batch of ethylene oxide catalyst from Example 1 is charged to an autoclave reactor and started up in the same manner as in Example 1. After about five days, operating conditions are changed to the same conditions favorable for AgCl formation as in Example 1. However, in this case no hydrogen sulfide is added to the reactor feed. The reactor is operated for about another 18 days and shut down. The catalyst is removed and analyzed. AgCl is not detected on the catalyst when analyzed by X-ray fluorescence and X-ray diffraction.

Example 6 and 7

Having recognizable and significant difference in geometric sizes, approximately equal amount i.e. 20 cc, of silver-based, non-rhenium and high efficiency rhenium-promoted ethylene oxide catalysts are charged to a smaller back-mixed reactor of the same general type as those employed in Examples 1-5. It is started up in the same manner as given in Example 1. Upstream of the reactor, the ethylene feed is desulfurized by contacting a guard bed of Selexsorb® CDX at ambient temperature and a pressure of about 340 psig (2340 kPa-gauge). The sulfur guard bed is made of a four and a half inch (11.4 cm) ID pipe with a length of about 25 inches (63.5 cm). The guard bed contains 1 gallon (3.8 liters) of Selexsorb® CDX. Based on the amount of sulfates found on the catalyst, as shown in Table 1 below, and the estimated percentage of feed gas sulfur that is adsorbed on the catalyst, it is estimated that the amount of sulfur in the feed gas on an atomic basis is about 15 ppbv following desulfurization in the sulfur guard bed. After about two days, operating conditions are changed to the same conditions favorable for AgCl formation as given in Example 1. At about the same time, a gas feed composing 0.05% of sulfur dioxide and balanced by helium with relative analytical uncertainty of ±2%, acquired from Airgas, is started to the reactor, corresponding to about 0.025 ppmv (25 ppbv) of sulfur dioxide based on the reactor feed flow rate. The reactor is operated for about 19 days and shut down. The charge is removed from the reactor and the two catalysts are separated. Example 6, i.e. non-rhenium catalyst contains 0.7 wt % AgCl, whereas Example 7, rhenium-promoted ethylene oxide catalyst contains 1.76 wt % AgCl. As summarized in Table 1 below the data indicates that silver-based, rhenium-promoted ethylene oxide catalyst is more vulnerable to sulfur-induced silver chloride formation.

Example 8 and 9

Similar to Example 6 and 7, a mixed-catalyst charge is prepared and introduced to a reactor. It is started up in the same manner as in Example 1. After about two days, operating conditions are changed to the same conditions favorable for AgCl formation as in Example 1. However, in this case, no sulfur compound, i.e. sulfur dioxide, is added to the reactor feed. The reactor is operated for about 19 days and shut down. The charge is handled in the same way as in Examples 6 and 7. AgCl is not detected on the catalyst when analyzed by X-ray fluorescence and X-ray diffraction.

TABLE 1

| Example | Type of Sulfur Compound Added to the Reactor Feed | AgCl on Catalyst after Shutdown (wt %) | AgCl Detected using XRD on Catalyst after Shutdown | $\Delta SO_4$ on catalyst (ppmw) |
|---|---|---|---|---|
| 1 | $H_2S$ | 1.75 | Detected | 295 |
| 2 | N/A | <0.1 | Not detected | 120 |
| 3 | $H_2S$ | 2.7 | Detected | 375 |
| 4 | $H_2S$ | 2.6 | Detected | 335 |
| 5 | N/A | <0.1 | Not detected | 60 |
| 6 | $SO_2$ | 0.7 | Detected | N/A |
| 7 | $SO_2$ | 1.76 | Detected | 340 |
| 8 | N/A | <0.1 | Not detected | N/A |
| 9 | N/A | <0.1 | Not detected | 125 |

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope. The scope of the invention is limited solely by the following claims.

What is claimed is:

1. A process for controlling the formation of silver chloride on a high-efficiency silver catalyst used in the production of an alkylene oxide from a reactor feed gas comprising an alkylene, oxygen, and at least one organic chloride, the process comprising controlling the concentration of sulfur in the reactor feed gas on an atomic basis to no more than about 50 ppbv.

2. The process of claim 1, wherein the step of controlling the concentration of sulfur in the reactor feed gas comprises selectively fluidly coupling at least one feed gas source to the process.

3. The process of claim 1, wherein the step of controlling the concentration of sulfur in the reactor feed gas on an atomic basis to not more than about 50 ppbv is carried out for at least two days.

4. The process of claim 1, wherein the step of controlling the concentration of sulfur in the reactor feed gas comprises providing an alkylene feed comprising the alkylene and sulfur-containing compounds, and desulfurizing the alkylene feed.

5. The process of claim 4, wherein the step of desulfurizing the alkylene feed comprises adsorbing at least a portion of the sulfur-containing compounds on an adsorbent bed.

6. The process of claim 5, wherein the adsorbent bed comprises a hydrogen sulfide adsorbing material.

7. The process of claim 5, wherein the adsorbent bed comprises a mercaptan-adsorbing material.

8. The process of claim 5, wherein the adsorbent bed comprises a sulfur-oxide adsorbing material.

9. The process of claim 5, wherein the adsorbent bed comprises a carbonyl sulfide adsorbing material.

10. The process of claim 5, wherein the step of desulfurizing the alkylene feed comprises converting at least a portion of the sulfur-containing compounds to hydrogen sulfide, and adsorbing at least a portion of the hydrogen sulfide on the adsorbent bed.

11. A process for manufacturing an alkylene oxide, comprising:
   providing an alkylene feed comprising at least one sulfur-containing compound;
   removing at least a portion of the at least one sulfur-containing compound from the alkylene feed to yield a desulfurized alkylene feed;
   combining the desulfurized alkylene feed with at least oxygen and at least one organic chloride to yield a reactor feed gas;
   controlling the concentration of sulfur in the reactor feed gas on an atomic basis to no more than about 50 ppbv; and
   reacting the reactor feed gas over a high efficiency silver catalyst to yield a reaction product comprising the alkylene oxide.

12. The process of claim 11, further comprising adjusting the rate of removal of the at least a portion of the at least one sulfur-containing compound from the alkylene feed to control the concentration of sulfur in the reactor feed gas.

13. The process of claim 11, wherein the step of removing at least a portion of the at least one sulfur-containing compound from the alkylene feed comprises adsorbing the at least a portion of the at least one sulfur-containing compound on an adsorbent bed.

14. The process of claim 13, wherein the step of controlling the concentration of sulfur in the reactor feed gas comprises adjusting an adsorbent bed temperature.

15. An alkylene oxide plant, comprising:
   a desulfurizing unit having an alkylene feed gas inlet and a desulfurized alkylene gas outlet; and
   an alkylene oxide reactor comprising a high efficiency silver catalyst bed, a reactor feed gas inlet, and an alkylene oxide product outlet, wherein the reactor feed gas inlet is fluidly coupled to the desulfurized alkylene gas outlet of the desulfurizing unit, an oxygen source, and an organic chloride source, and the plant is configured to control the concentration of sulfur in the reactor feed gas on an atomic basis to no more than about 50 ppbv.

16. The alkylene oxide plant of claim 15, further comprising an alkylene oxide reactor feed gas sulfur controller configured to control the concentration of at least one sulfur-containing compound in the reactor feed gas such that the concentration of sulfur in the reactor feed gas on an atomic basis is less than about 50 ppbv.

17. The alkylene oxide plant of claim 15, wherein the desulfurizing unit comprises a sulfur conversion unit fluidly coupled to a hydrogen sulfide adsorbent bed, the sulfur conversion unit comprises the alkylene feed gas inlet, and the hydrogen sulfide adsorbent bed comprises the desulfurized alkylene gas outlet.

18. The alkylene oxide plant of claim 15, wherein the high efficiency silver catalyst is rhenium promoted.

19. The alkylene oxide plant of claim 15, further comprising a heavy hydrocarbon contaminant pretreater comprising a heavy-hydrocarbon contaminated alkylene feed inlet and a decontaminated alkylene product outlet, wherein the decontaminated alkylene product outlet is fluidly coupled to the alkylene feed gas inlet of the desulfurizing unit.

20. The alkylene oxide plant of claim 15, wherein the desulfurizing unit is a first desulfurizing unit, the plant further comprises a feed pretreater, and the feed pretreater comprises a heavy hydrocarbon contaminant pretreater, the first desulfurizing unit and a second desulfurizing unit.

* * * * *